US011883169B2

(12) United States Patent
Fedoruk et al.

(10) Patent No.: US 11,883,169 B2
(45) Date of Patent: Jan. 30, 2024

(54) OPENER FOR SECURE SAMPLE COLLECTION BOTTLE

(71) Applicants:Major League Baseball Properties, Inc., New York, NY (US); US Anti-Doping Agency (USADA), Colorado Springs, CO (US)

(72) Inventors: Matthew Fedoruk, Colorado Springs, CO (US); Jon Coyles, New York, NY (US); Sandi Briggs, Colorado Springs, CO (US); Tylor Garland, Los Angeles, CA (US); Stephen Bradford, Los Angeles, CA (US); Cezanne Farris-Gilbert, Los Angeles, CA (US); Michael Latham, Los Angeles, CA (US); Robert Reich, Los Angeles, CA (US); Andrew Castro, Los Angeles, CA (US); Elliott Davis, Los Angeles, CA (US); David N. Huang, Los Angeles, CA (US); Will Song, Los Angeles, CA (US); Shane Baxley, Los Angeles, CA (US); Ryan Cohn, Los Angeles, CA (US)

(73) Assignee: INNOVERO LLC, Colorado Springs, CO (US)

( * ) Notice: Subject to any disclaimer, the term of this patent is extended or adjusted under 35 U.S.C. 154(b) by 1301 days.

(21) Appl. No.: 16/376,751

(22) Filed: Apr. 5, 2019

(65) Prior Publication Data

US 2019/0308864 A1 Oct. 10, 2019

Related U.S. Application Data

(60) Provisional application No. 62/789,896, filed on Jan. 8, 2019, provisional application No. 62/760,640, filed
(Continued)

(51) Int. Cl.
*A61J 1/14* (2023.01)
*B01L 9/00* (2006.01)
(Continued)

(52) U.S. Cl.
CPC ...... *A61B 5/150343* (2013.01); *A61B 10/007* (2013.01); *A61J 1/1412* (2013.01);
(Continued)

(58) Field of Classification Search
None
See application file for complete search history.

(56) References Cited

U.S. PATENT DOCUMENTS 2,671,959 A * 3/1954 Silberhorn ............... B67B 7/30
30/1.5
3,954,030 A * 5/1976 Newton .................. B67B 7/00
D8/18
(Continued)

*Primary Examiner* — Paul S Hyun
(74) *Attorney, Agent, or Firm* — Leason Ellis LLP

(57) ABSTRACT

A system for opening a secure specimen sample bottle includes a base having a first area and a first raised hollow portion for receiving and holding the specimen sample bottle. The first raised hollow portion has a groove formed along an outer surface thereof. The system includes a cutter for cutting a first portion of the specimen sample bottle. The cutter has a handle at a first end and a second end portion that receives the first portion of the specimen sample bottle and a blade for cutting the first portion. The second end portion has a flange with a raised rail formed along an inner surface of the flange, with the raised rail being received within the groove to couple the cutter to first raised portion during performance of a cutting operation.

12 Claims, 34 Drawing Sheets

Related U.S. Application Data on Nov. 13, 2018, provisional application No. 62/653,305, filed on Apr. 5, 2018.

(51) Int. Cl.

| | |
|---|---|
| B67B 7/46 | (2006.01) |
| A61B 5/15 | (2006.01) |
| B65B 69/00 | (2006.01) |
| B01L 3/00 | (2006.01) |
| *A61B 10/00* | (2006.01) |
| *B65D 41/34* | (2006.01) |
| *G01N 1/00* | (2006.01) |
| *B65D 55/02* | (2006.01) |
| *B65D 49/12* | (2006.01) |

(52) U.S. Cl.
CPC ............... B01L 3/508 (2013.01); B01L 9/00 (2013.01); B65B 69/0033 (2013.01); B67B 7/34 (2013.01); *A61B 5/150351* (2013.01); *B01L 2200/025* (2013.01); *B01L 2200/141* (2013.01); *B01L 2300/042* (2013.01); *B01L 2300/0609* (2013.01); *B01L 2300/0672* (2013.01); *B65D 41/3404* (2013.01); *B65D 49/12* (2013.01); *B65D 55/022* (2013.01); *B65D 2255/20* (2013.01); *G01N 2001/007* (2013.01); *Y10S 206/807* (2013.01); *Y10S 215/901* (2013.01)

(56) References Cited

U.S. PATENT DOCUMENTS

| | | | |
|---|---|---|---|
| 4,563,818 A | * | 1/1986 | Kreth .................. B67B 7/34 30/426 |
| 4,813,563 A | | 3/1989 | Ogden et al. |
| 5,325,980 A | | 7/1994 | Grimm et al. |
| 5,690,246 A | | 11/1997 | Anderson et al. |
| 2004/1320911 | | 7/2004 | Ramsey et al. |
| 2017/0239651 A1 | | 8/2017 | Higgins |

\* cited by examiner

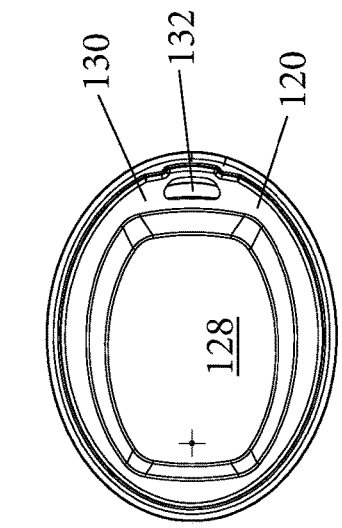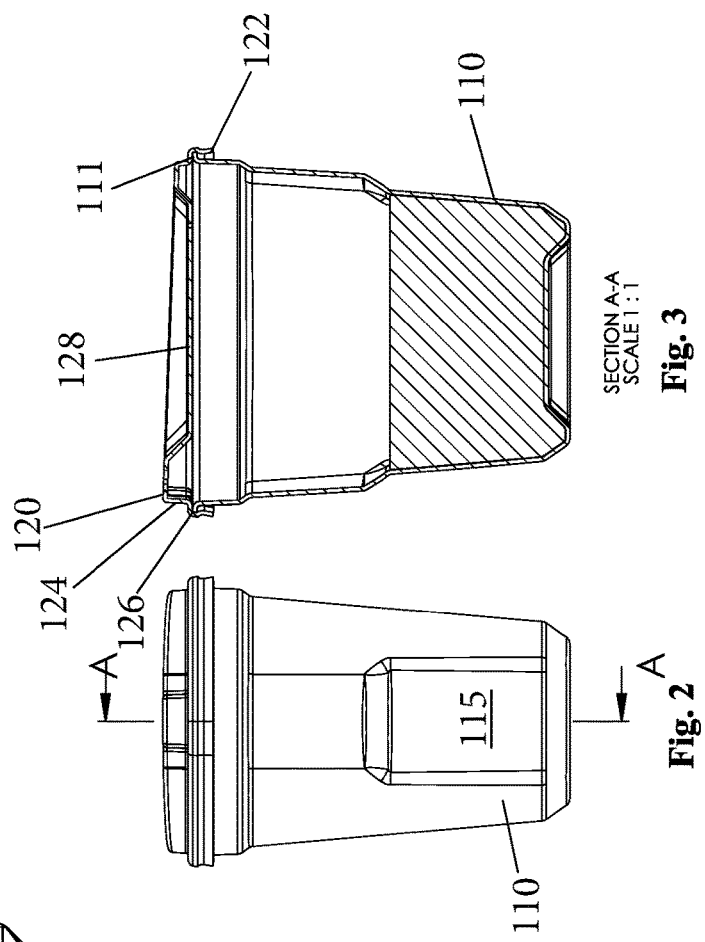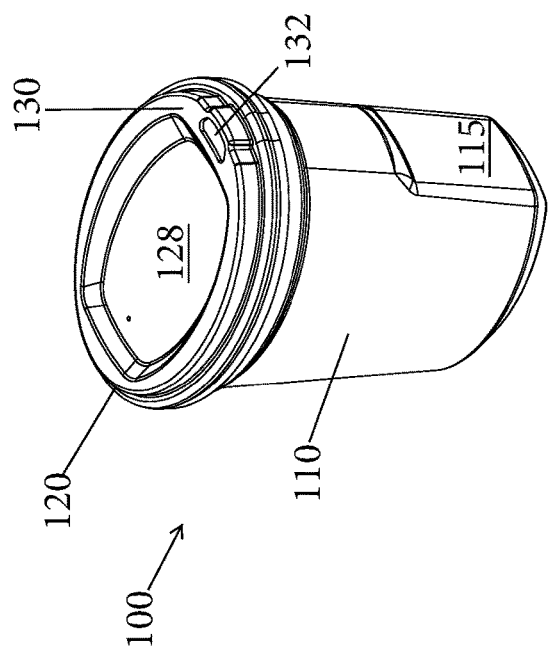

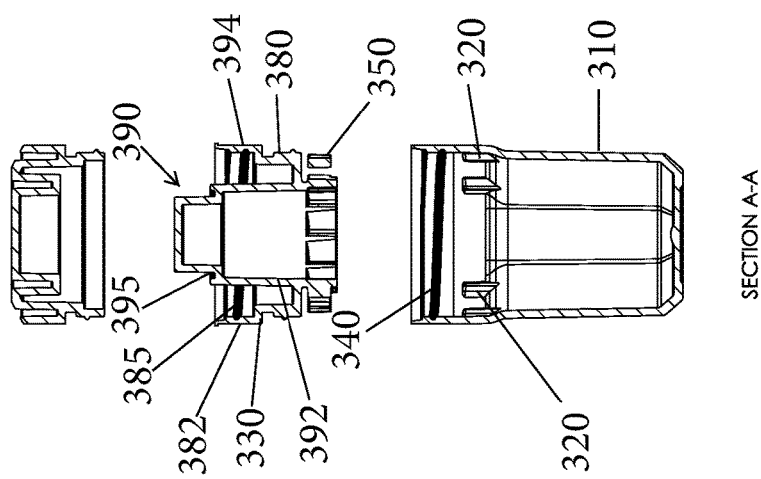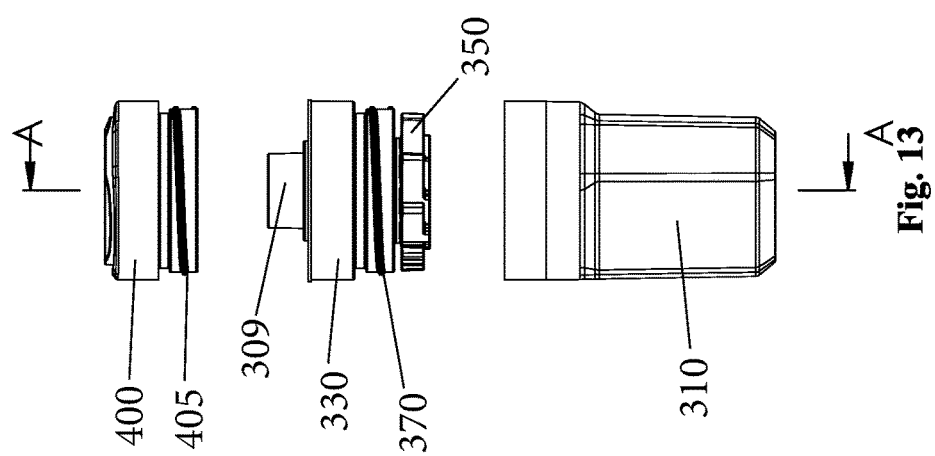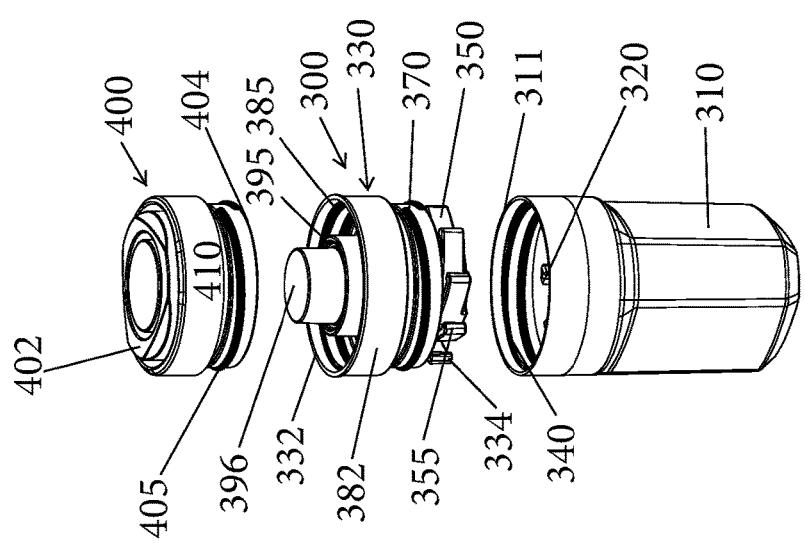

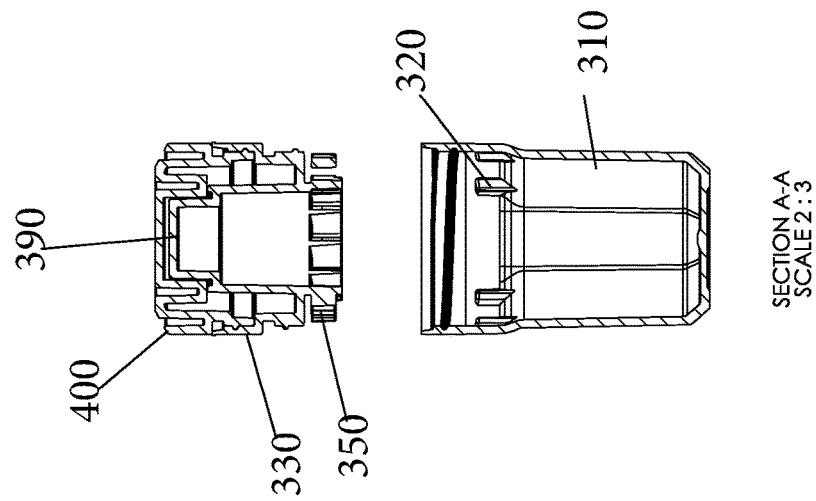
Fig. 17
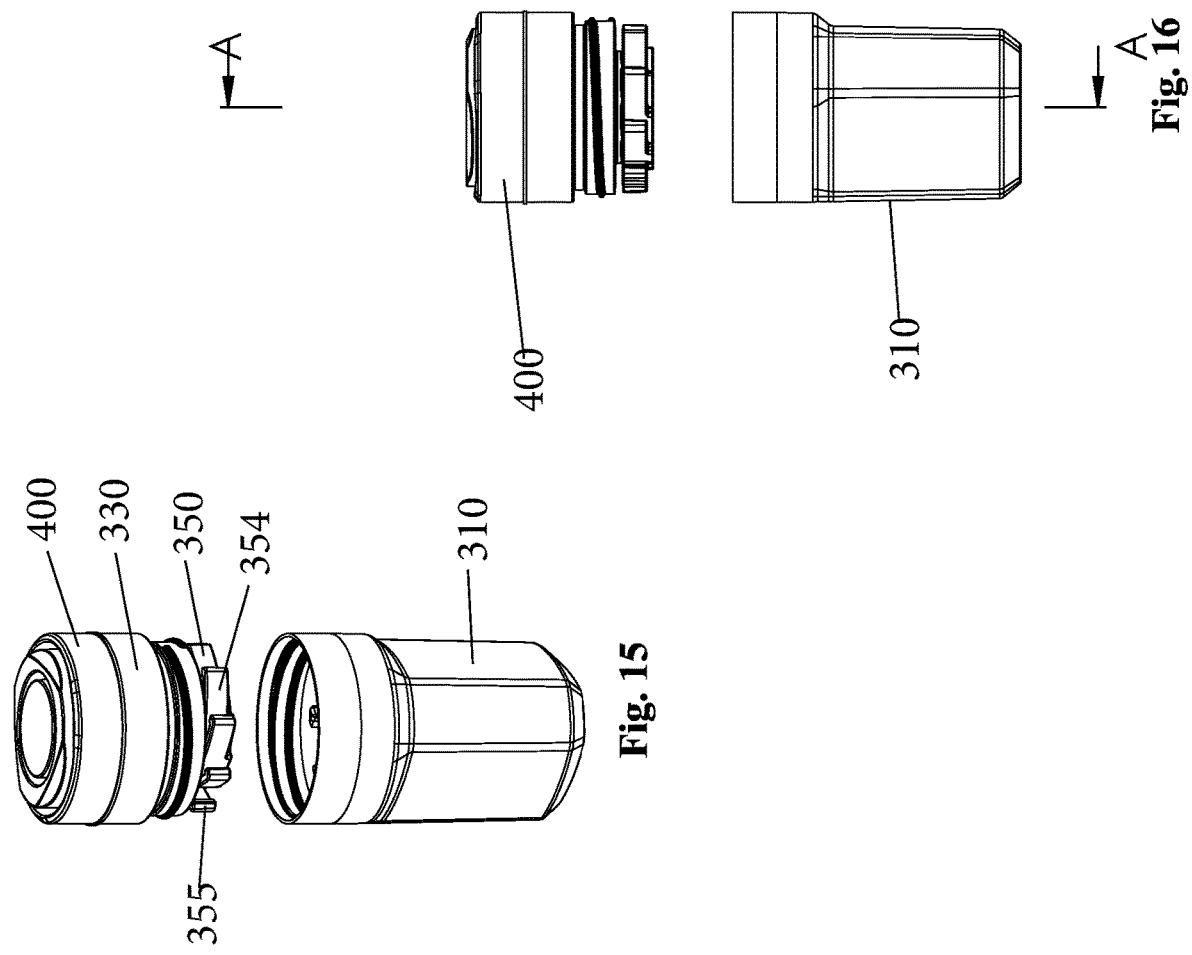
Fig. 16
Fig. 15

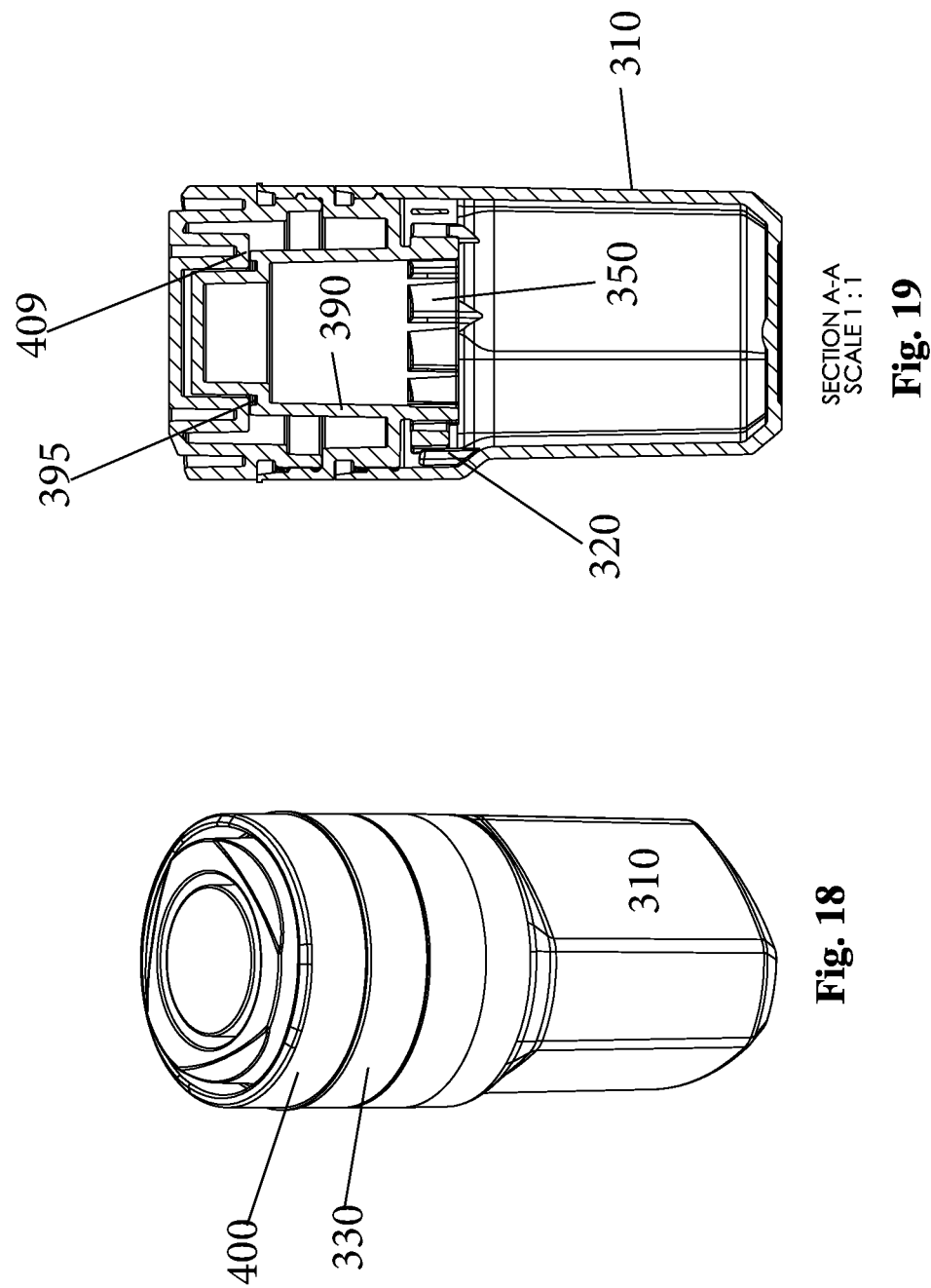

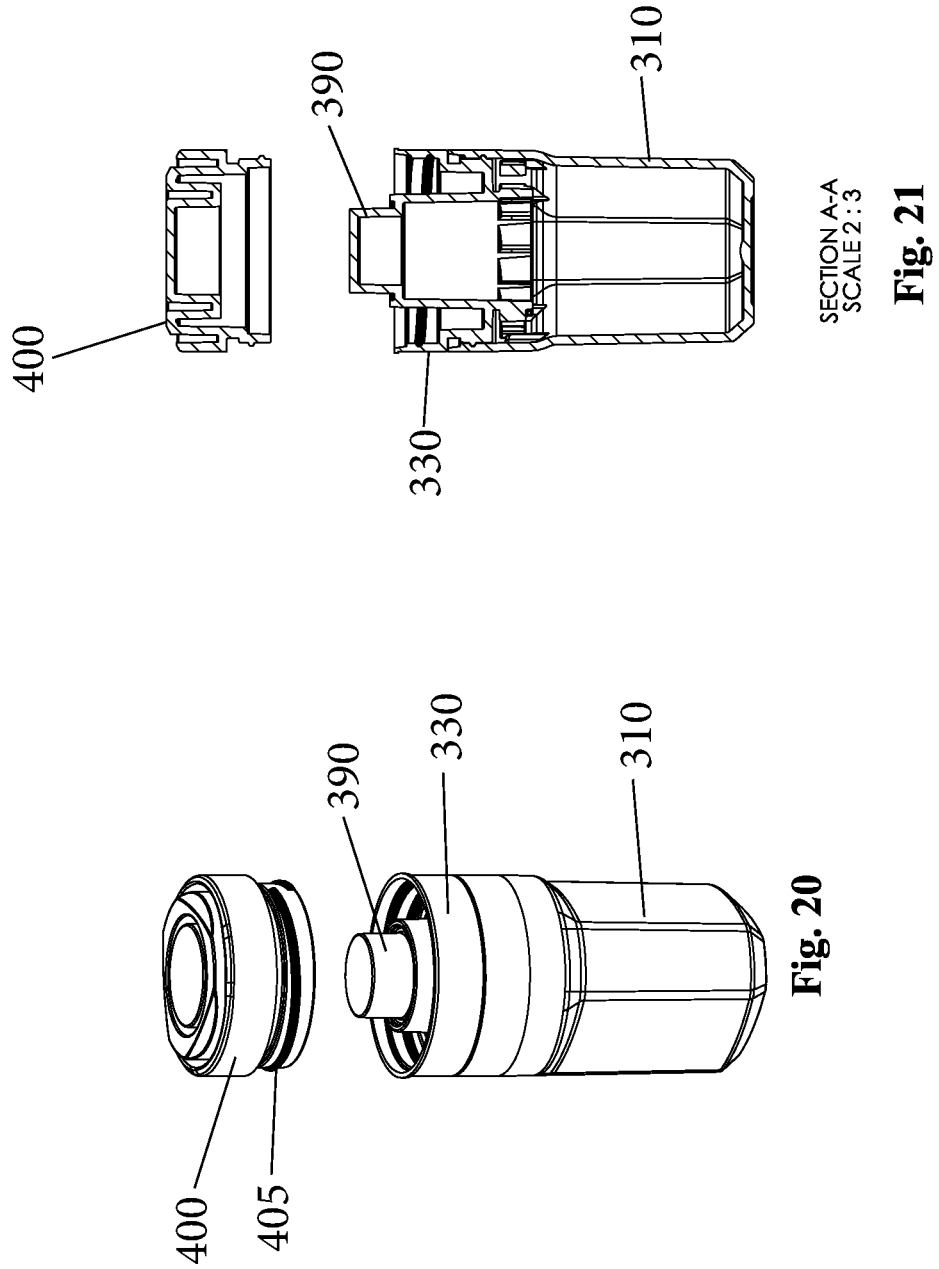

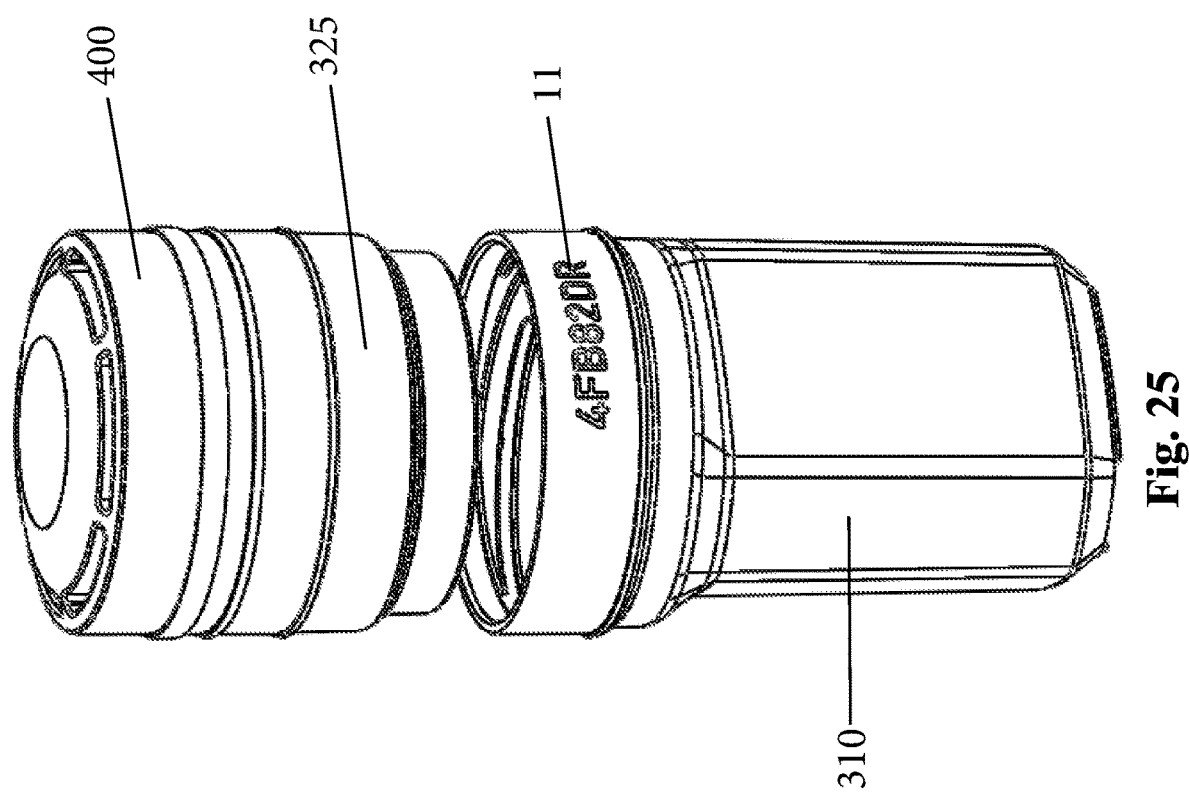

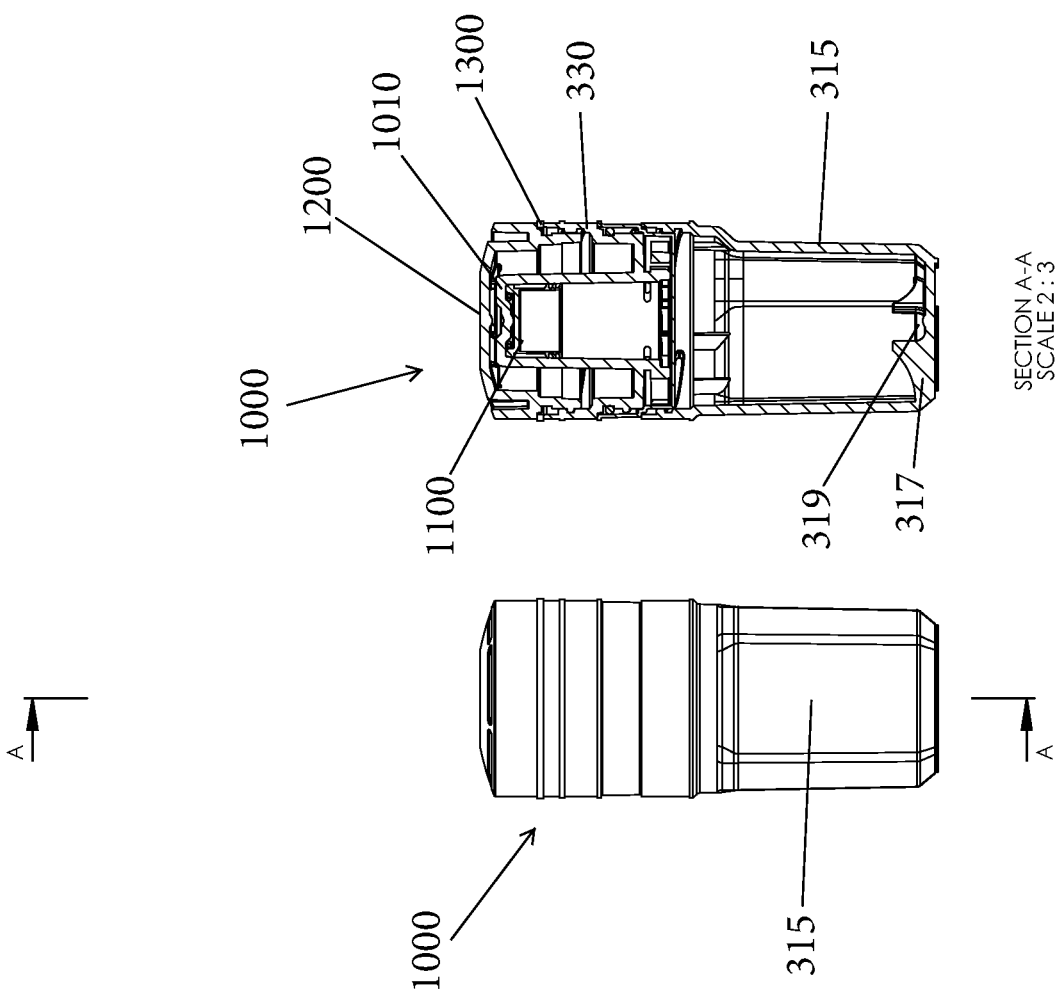

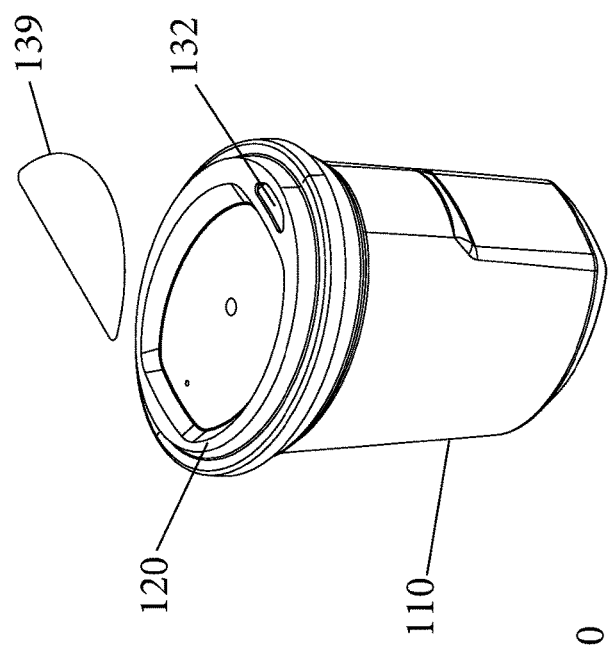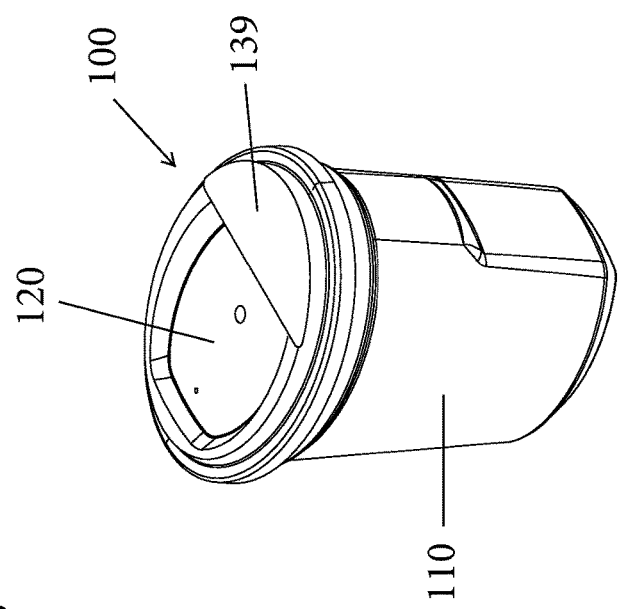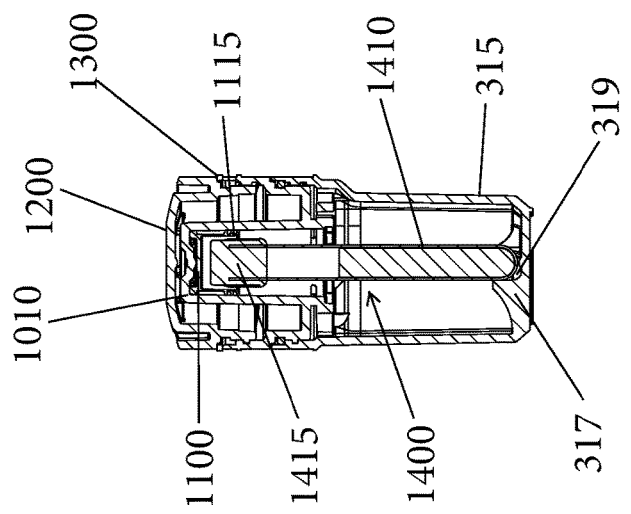

OPENER FOR SECURE SAMPLE COLLECTION BOTTLE

CROSS REFERENCE TO RELATED APPLICATIONS

The present application claims priority to and the benefit of U.S. patent application Ser. No. 62/653,305, filed Apr. 5, 2018, U.S. patent application Ser. No. 62/760,640, filed Nov. 13, 2018, and U.S. patent application Ser. No. 62/789,896, filed Jan. 8, 2019, each of which is hereby incorporated by reference in its entirety.

TECHNICAL FIELD

The present invention relates to liquid collection bottles and more particularly, relates to a collection bottle and collection kit for receiving and storing a bodily fluid, such as urine or blood, in a secure, tamper-proof manner and additionally, relates to a processing (lab intake) system for opening the collection bottle and recording unique identification data associated with the collection bottle, as well as security and tracking features related to the collection bottle and other parts of the collection kit.

BACKGROUND

Drug testing is the evaluation of a urine, blood or other type of biological sample to determine if the subject has been using the drug or drugs in question. There are many circumstances that may lead to drug testing including but not limited to the following: (1) pre-employment drug screening test or random, work-related drug testing to identify on-the-job drug abuse; (2) college or professional athletic drug testing; (3) post-accident drug testing—a vehicular or on-the-job accident which may have involved human error and resulted in casualties or property damage; and (4) safety-related drug testing—if an employee's job could lead to safety issues if judgement or physical ability were impaired.

With respect to amateur or professional athletes, drug testing will part a part of the athlete's life as long as he/she chooses to compete at an elite level. This testing ensures the integrity of the sport and is critical in the global fight for a clean sport. Given that much is on the line, there are strict procedures and protocols for taking a fluid sample (e.g., blood or urine sample) from the athlete and then processing and testing the sample. For an athlete or worker, the drug testing may not be announced, while in other settings, such as applying for a new job, the drug testing will be known about by the job applicant.

Typically, when it is time to provide a sample, the person will either have been given a sealed collection vessel or the person will be asked to select a sealed sample collection vessel from a choice of vessels. The person should check and inspect the collection vessel to ensure that it has not been tampered with and will be instructed to rinse their hands with only water before opening the vessel. The person will be asked to provide a urine sample of at least a prescribed quantity and typically under direct observation of a witnessing chaperone of the same gender. The vessel has a unique identifier and is sealed and in the event that the specimen must be transported to an outside laboratory, it should be mailed in a sealed container and placed in an external carton with an evidence seal. Chain of custody is of paramount importance in the processing and testing of the specimens and thus, it is critical that the specimen collection equipment, as well as the collection and testing protocol, are tamper proof.

The present invention is directed to providing improved specimen (sample) collection equipment including but not limited to the collection vessels that hold the specimen.

SUMMARY

In one aspect, the present invention relates to equipment and stations that are configured to process and open a secure sample collection bottle in a controlled manner. In one embodiment, a system for opening a secure specimen sample bottle includes a base having a first area and a first raised hollow portion for receiving and holding the specimen sample bottle. The first raised hollow portion has a groove formed along an outer surface thereof. The system includes a cutter for cutting a first portion of the specimen sample bottle. The cutter has a handle at a first end and a second end portion that receives the first portion of the specimen sample bottle and a blade for cutting the first portion. The second end portion has a flange with a raised rail formed along an inner surface of the flange, with the raised rail being received within the groove to couple the cutter to first raised portion during performance of a cutting operation.

A method for opening a secure specimen sample bottle includes the step of placing the specimen sample bottle within a holder. The specimen sample bottle includes a base receptacle, a lock ring that interlockingly mates with the base receptacle so as to prevent removal of the lock ring from the base receptacle and prevent access to a specimen contained in the base receptacle, and a removable cap that is coupled to the lock ring. The lock ring includes an upstanding hollow spire structure. The hollow spire structure is exposed above the holder. The method further includes the steps of removing the cap and cutting spire structure so as to separate a closed top end portion of the spire structure from a bottom portion thereof. The closed top end portion of the spire structure is then removed to permit access to the specimen for testing thereof.

BRIEF DESCRIPTION OF THE DRAWING FIGURES

FIG. 1 is a perspective view of a collection cup (first receptacle) for collecting a fluid, such as a liquid bodily fluid;

FIG. 2 is a side elevation view thereof;

FIG. 3 is a cross-sectional view taken along the line A-A;

FIG. 4 is a top plan view thereof;

FIG. 12 is an exploded perspective view of a sample bottle assembly according to a first embodiment;

FIG. 13 is an exploded side elevation view thereof;

FIG. 14 is a cross-sectional view taken along the line A-A of FIG. 13;

FIG. 15 is an exploded perspective view of the sample bottle assembly in a partially assembled condition;

FIG. 16 is an exploded side elevation view thereof;

FIG. 17 is a cross-sectional view taken along the line A-A of FIG. 16;

FIG. 18 is a perspective view of the sample bottle assembly in a fully assembled condition;

FIG. 19 is a cross-sectional view thereof;

FIG. 20 is an exploded perspective view of the sample bottle assembly with a lock ring being coupled to a sample bottle and a cap being removed therefrom;

FIG. 21 is a cross-sectional view thereof;

FIG. 25 is an exploded perspective view showing a lock ring protector that can be provided for packaging and transportation of the sample bottle assembly;

FIG. 32 is a side elevation view of a collection bottle assembly according to another embodiment in a fully assembled condition;

FIG. 33 is a cross-sectional view thereof;

FIG. 44 is a cross-sectional view thereof in a fully assembled condition;

FIGS. 45-46 are perspective views of a hygienic seal member used to cover the spout opening the collection cup.

DETAILED DESCRIPTION OF CERTAIN EMBODIMENTS

Figure 7:
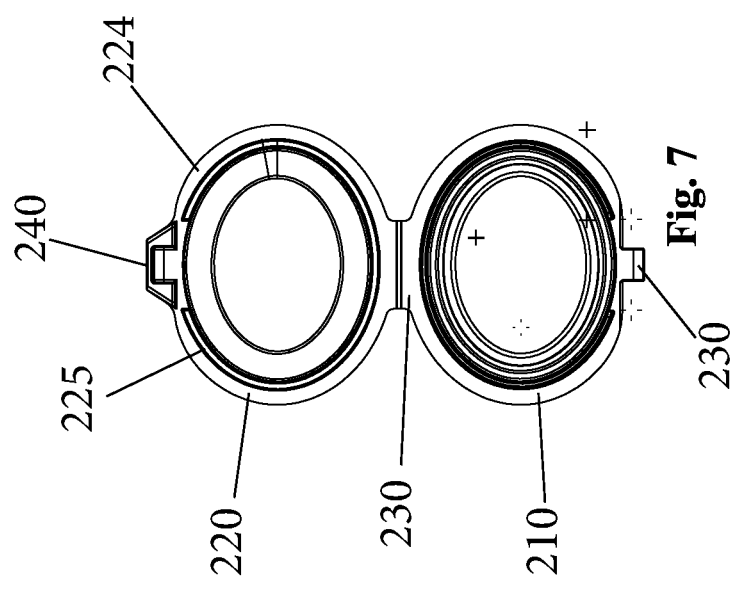
FIG. 7 is a top plan view thereof with the lid opened.

The present invention is directed to a fluid collection system and more particularly, a fluid collection system for collecting and securely holding a bodily fluid, such as urine or blood. As described herein, the fluid collection system comprises a number of different parts that complement one another and are intended for use in collection of a bodily fluid from a person. As is well understood, in many different professions, including but not limited to transportation employees and professional/amateur athletes, it is mandatory for the individual to undergo drug testing. Most drug testing involves the collection of a urine and/or blood sample from the individual and then processing and analyzing the sample to detect the presence of any banned substances.

As one can imagine, with so much on the line, some people try to cheat the system by tampering with or otherwise fraudulently submitting another sample other than from the individual being tested. While there are a series of controls in place including supervision and chain of custody, there unfortunately is a small number of individuals that try to falsify the results by manipulating the process, such as by having an inside person switch samples, etc. The term "chain of custody" generally refers to a document or paper trail showing the seizure, custody, control, transfer, analysis, and disposition of physical and electronic evidence of a human specimen test.

The present invention is directed to an improved collection bottle and sample collection kit and an overall improved sample collection protocol that addresses and overcomes the deficiencies associated with traditional fluid collection bottles as well as the traditional fluid collection protocol.

In addition, the present invention is directed to equipment, such as an opener, for opening the sample collection bottle to allow controlled access to the specimen. It will be appreciated that the sample collection bottle assembly and the other parts described herein can be arranged in kit format. In other words, the individual parts can be provided and packaged as a kit.

Collection Cup

FIGS. 1-4 illustrate a collection cup (first receptacle) 100 for collecting a fluid, such as a liquid bodily fluid (e.g., urine). The collection cup 100 comprises a base or cup body (receptacle) 110 and a lid or cover 120. The cup body 110 is a hollow structure that is meant to receive and hold the liquid sample (e.g., urine). The cup body 110 can be formed of any number of different materials, such as different plastics, and in one embodiment, is formed of an injection moldable material. The cup body 110 is preferably formed of a transparent material to allow easy viewing of the liquid sample that is contained therein. As shown, the cup body 110 can be contoured to have an outwardly flared top portion that has a larger diameter than a bottom portion of the cup body. A top edge 111 of the cup body 110 can comprise an outwardly flared lip. Along sides (ends) of the cup body 110, a pair of recessed portions 115 with planar floor sections can be formed to provide opposing surfaces along which the individual can securely grasp and hold the cup body 110. Along the side of the cup body 110 is measurement indicia, such as measurement (volume) graduations. A minimum fill line, such as 90 ml, can be clearly indicated on the cup body 110.

The cup body 110 can be formed to have any number of different shapes including an oval shape as shown.

The lid 120 is intended to be securely attached to the top of the cup body 110 and in one embodiment, the lid 120 and cup body 110 mate together via a snap-fit type attachment. The lid 120 has an outer peripheral wall 122 that is configured to mate with the lip 111 of the cup body 110 to form a snap-fit attachment between the lid 120 and the cup body 110. The lid 120 has a stepped construction in that there is an inner wall 124 that is spaced inward relative to the outer peripheral wall 122 with a transverse (horizontal) wall 126 connecting the walls 122, 124 so as to form a shoulder between the two walls 122, 124. Along a top surface of the lid 120, a recessed portion 128 can be formed and at one end of the lid 120, there can be a raised portion 130 that includes an opening (spout opening) 132 which permits easy pouring of the liquid sample contained within the cup body 110. The opening 132 can have an oval shape that is ergonomic for both men and women.

The lid 120 thus snaps on securely and provides clean and controlled pouring while the hygienic seal protects from the contamination. The fluid levels and minimum fill level are clearly marked to improve ease of use. The hygienic seal can be any number of different seal members that serve the intended function.

FIGS. 45-46 depict another aspect of the claimed invention in that a hygienic seal member 139 can be used to cover the spout opening 132. The seal member 139 can be formed of any number of different materials and can include an adhesive means for being detachably attached to the lid 120 to cover the spout opening 132. After the sample is delivered to the cup body 110, the lid 120 is attached with the seal member 139 intact. The spout structure including the spout opening 132 are thus protected from contaminants and once, it is ready to transfer the sample from the cup body 110 to another receptacle, such as the sample bottle, discussed below, the seal member 139 is removed, thereby opening up the spout opening 132 and the sample is poured through the spout opening 132.

Partial Sample Storage Receptacle

Figure 5:
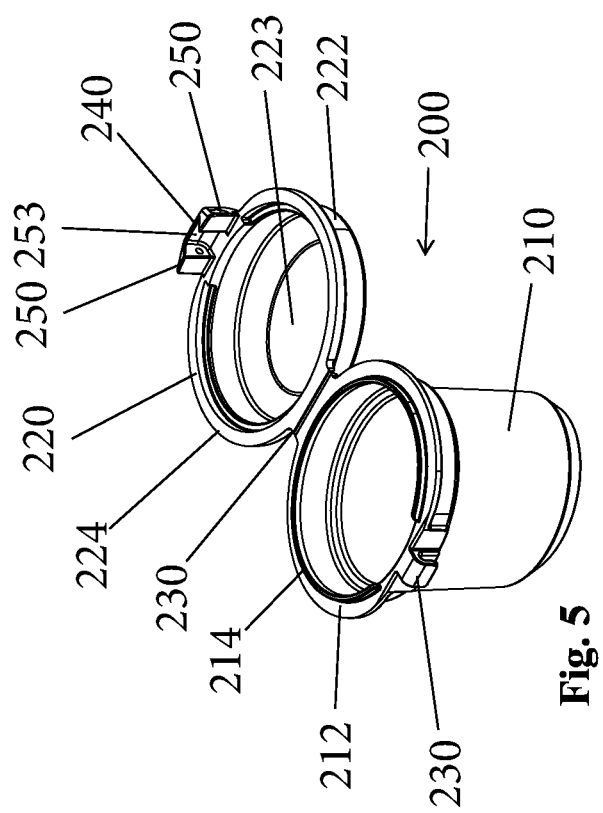
FIG. 5 is a perspective view of a partial sample storage receptacle.
Figure 6:
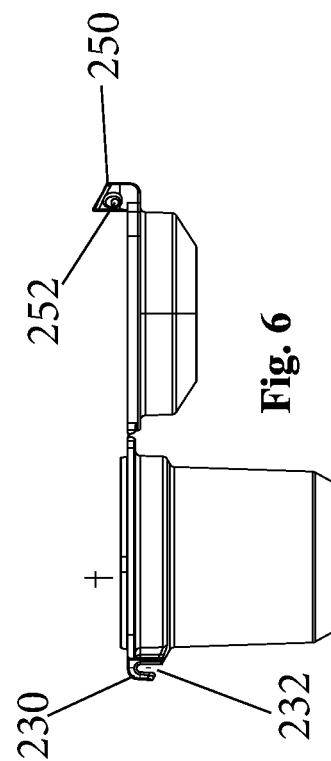
FIG. 6 is a side elevation view thereof with a lid opened.
Figure 9:
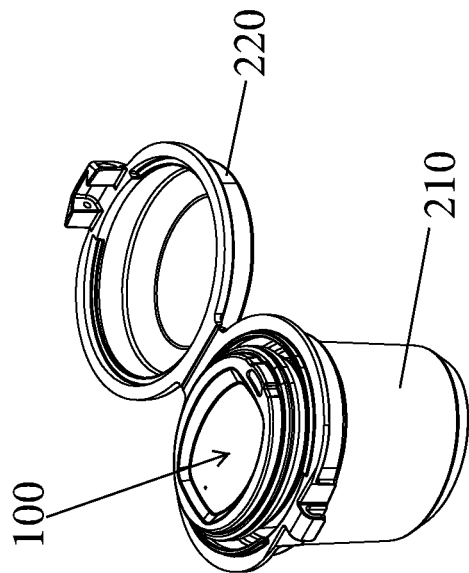
FIG. 9 is a perspective view showing reception of the collection cup into the storage receptacle with the lid open.
Figure 8:
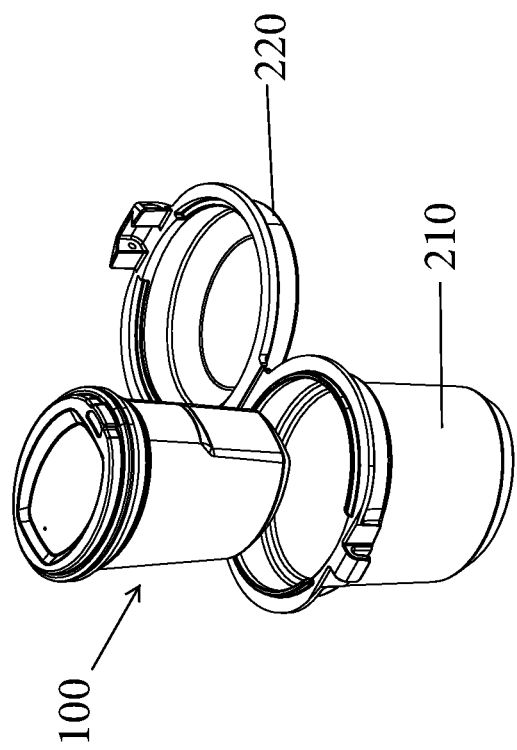
FIG. 8 is an exploded perspective view showing the collection cup for reception into the storage receptacle with the lid open.

With reference to FIGS. 1-11, in the event that an individual is unable to provide the minimum amount of fluid, the lid 120 is secured to the cup body 110 and is then placed into a protective covering (not shown), such as an opaque plastic biohazard bag. The bag is then sealed to resist contamination and it is then placed into a reusable partial sample storage receptacle 200 (FIG. 5). The receptacle 200 is thus configured to receive and hold the cup body 110 and lid 120.

The receptacle 200 includes a cup body 210 and a lid or cover 220 that is connected to the cup body 210 by a living hinge 230. The cup body 210 thus has a closed bottom and an open top that includes a top edge 212. In one embodiment, the top edge 212 can be a flat (planar) surface along which a raised ridge 214. The raised ridge 214 does not extend completely around the top edge 212 but instead a break is formed toward a front of the cup body 210.

As with the cup body 110, the cup body 210 can be contoured to have an outwardly flared top portion that has a larger diameter than a bottom portion of the cup body. The cup body 210 further includes a locking hook 230 that can be in the form of a downwardly extending J-shaped hook with a slot or space 232 being defined therein.

The lid 220 includes a peripheral side wall 222 and a top wall 223 that extends between the peripheral side wall 222 and closes off the lid 220. The lid 220 has a bottom edge 224 as well as an inner ledge 225 located radially inward of the bottom edge 224. When the lid 220 is in the closed position, the bottom edge 224 seats against the top edge 212 and the raised ridge 214 is received within the inner surface of the bottom edge 224 and seats against the inner ledge 225 to result in a sealed closure between the lid 220 and the cup body 210.

The lid 220 includes a locking latch 240 that extends outwardly and downwardly from the bottom edge 224. The latch 240 has a pair of side portions (lobes) 250 each of which includes a hole 252 passing therethrough and being axially aligned with respect to one another. The center portion 253 of the latch 240 is open to allow for reception of the hook 230 when the lid 220 is closed. As shown in the figures, once the lid 220 is closed relative to the cup body 210, the two side portions 250 are disposed on either side of the hook 230 and the holes 252 are located within the space 232 such that they are freely in communication with one another.

Figure 11:
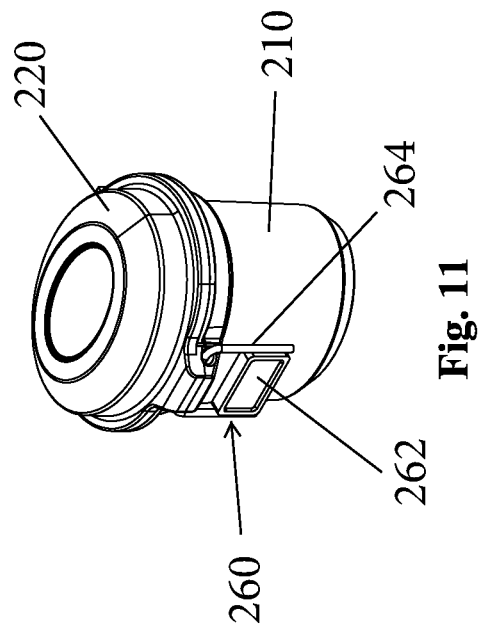
FIG. 11 is a perspective view of the storage receptacle in the closed position with a lock tag being attached.
Figure 10:
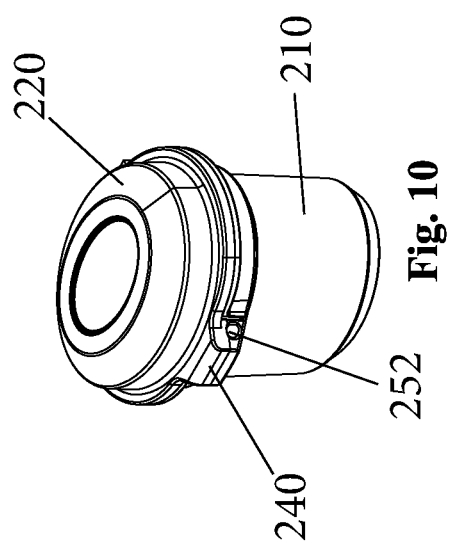
FIG. 10 is a perspective view of the storage receptacle in the closed position.

Once the lid 220 is closed, the receptacle 200 is locked using a lock tag 260 (FIG. 11). The lock tag 260 includes an identification section 262 on which a unique ID can be printed and a wire portion 264 that passes through the hole 252 of one side portion 250 across the space 232 and through the hole 252 of the other side portion 250. This unique ID is then added to a control record (chain of custody records). The lock tag 260 can be a one-time-use lock. It will be appreciated that the unique ID can take any number of different forms including but not limited to printed indicia, such as a series of numbers, letters, or a combination thereof; machine readable code (e.g., a bar code or RFID code), etc.

The hollow interior of the cup body 210 is shaped and sized to receive the cup body 110. Thus, after the collection cup 100 is sealed, it is placed into this hollow interior of the cup body 210 as shown in the figures.

Sample Bottle

Now referring to FIGS. 12-22, after a sufficient amount of liquid sample is collected in the collection cup 100, the liquid sample is then transferred to a sample bottle assembly 300 according to a first embodiment of the present invention. The sample bottle assembly 300 is formed of a number of individual, discrete parts that are assembled to form the sample bottle assembly 300. The sample bottle assembly 300 includes a sample bottle 310 that can be formed of an injection moldable material and can be transparent. The sample bottle 310 can include an outwardly flared top portion and a bottom portion that has a diameter less than the top portion.

Figure 22:
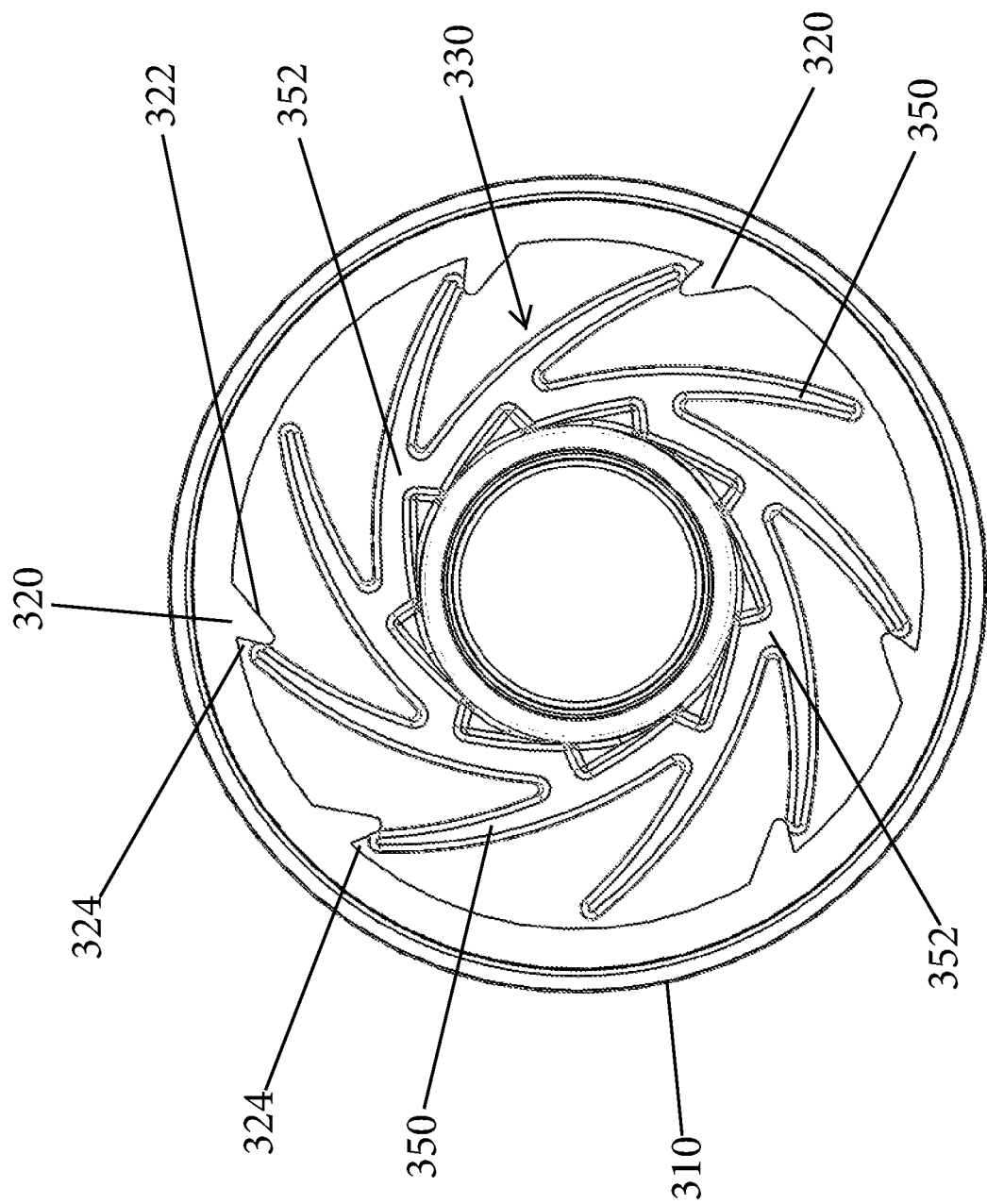
FIG. 22 is a top plan view showing engagement between the lock ring and the sample bottle.
Figure 24:
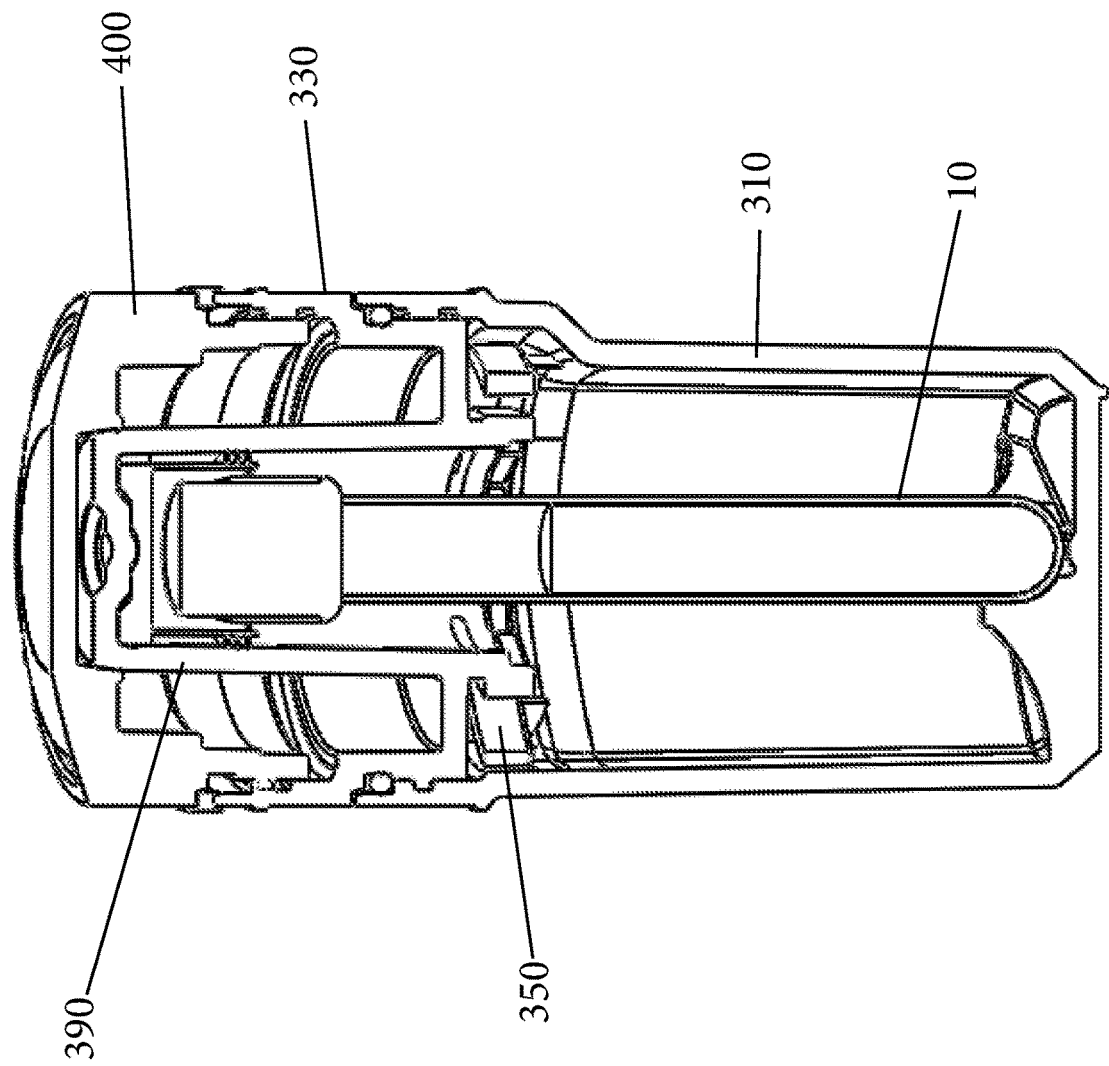
FIG. 24 is a perspective view in partial cross-section of the blood adapter kit in a closed position.
Figure 23:
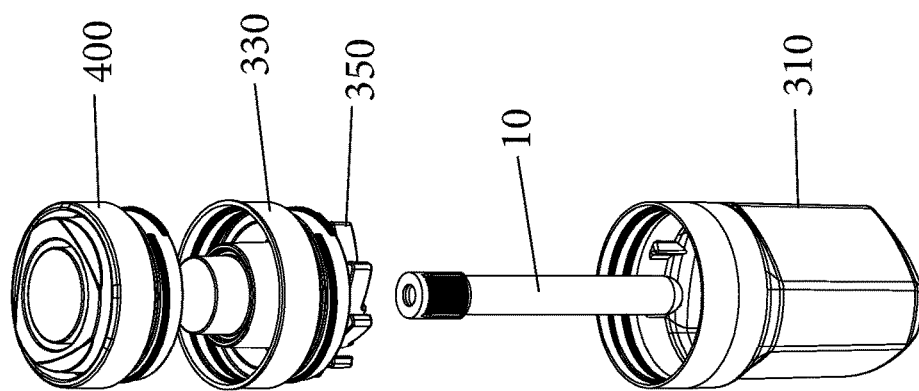
FIG. 23 is an exploded perspective view of a blood adapter kit.

The sample bottle 310 has a top edge 311 at the open end thereof. Along the inner surface of the sample bottle 310, there is a plurality of teeth 320 that are spaced circumferentially apart from one another. While, it is preferred that there be a plurality of teeth 320, it will be appreciated that the sample bottle 310 could be constructed such that there is only a single tooth 320 used to lock the bottle 310 as described herein with respect to the plurality of teeth 320. As shown in FIG. 22, the teeth 320 are integrally formed with the side wall of the sample body 310 and include an angled or swept surface (cam surface) 322 and a lock surface 324. As illustrated, the lock surface 324 can be a planar surface. The teeth 320 all face in the same direction, in that the direction of the angled surface 322 is the same for all of the teeth 320. In one embodiment, there are six (6) teeth 320 that are formed as part of the sample bottle 310. As shown, the teeth 320 can be formed in the outwardly flared top portion of the sample bottle 310. Between the top edge 311 and the teeth 320, inner threads 340 are formed. Alternatively, the locking mechanism (teeth) can be formed above the threads.

The sample bottle assembly 300 further comprises a lock ring component (lock ring) 330 that is configured to irreversibly lock to the sample bottle 310, thereby preventing a person from gaining unauthorized access to the contents of the sample bottle 310.

The lock ring 330 has a number of different sections each of which is described below. The lock ring 330 has a first end 332 and an opposite second end 334 that is configured for insertion into the hollow interior of the sample bottle 310. At the second end 334, a plurality of flexible fins 350 are formed. Each fin 350 extends radially outward from a center core 352 that has a hollow center that communicates with the hollow interior of the sample bottle 310. As shown, each fin 350 extends outwardly from the core 352 at an angle other than 90 degrees. The fins 350 are flexible and are configured to mate with the teeth 320 in a ratchet-like manner. As is known, a ratchet is a mechanical device that allows continuous linear or rotary motion in only one direction while preventing motion in the opposite direction.

As shown in the figures, the fins 350 interlockingly and selectively engage the teeth 320. Since there are nine fins 350 and six teeth 320, not all of the fins 350 engage the teeth 320. Thus, in the locked position of the lock ring 330, described herein, three of the fins 350 are free of engagement with the teeth 320. As will be appreciated, the direction of curvature of the fins 350 and the angled surfaces 322 are complementary so that the fins 350 ride along the angled (cam) surfaces 322 until the fins 350 reach the end of the angled surfaces 322 at which time, the fins 350 flex outward and the distal ends of the fins 350 seat against the lock surface 324. This action prevents rotation of the lock ring 330 in one direction relative to the sample bottle 310.

In one embodiment, above the fins 350, the lock ring 330 includes first threads 370 that are configured to threadingly mate with the inner threads 340 of the sample bottle 310. It will be appreciated that the location above the fins 350 is only exemplary and other locations are equally possible. The first threads 370 are formed along an outer surface of an outer peripheral side wall 380 and more particularly, is formed along the outer surface of a bottom section of the outer peripheral side wall 380. The outer peripheral side wall 380 also includes a top section that can have a smooth outer surface 382 on which unique ID indicia (discussed hereinbefore) can be formed. The top section has a larger diameter relative to the bottom section and therefore, a stepped construction is formed and a right angle shoulder is formed between the top and bottom sections. Along an inner surface of the top section, second threads 385 are formed.

Internal to the lock ring 330, there is a hollow spire structure 390 that extends upwardly from the core 352 and protrudes above a top edge of the top section of the outer peripheral side wall 380. The spire structure 390 also has a variable diameter in that a bottom portion 392 has a larger diameter than a top portion 394 thereof. At an interface between the top portion 394 and the bottom portion 392, there is a landing in which an annular shaped channel 395. An O-ring is disposed within this channel 395 in order to establish a seal as discussed below. The channel 395 can be located within the plane of the top edge of the top portion 394 or can be located slightly above this plane. A top of the top portion 394 is closed off by a top wall 396. In the alternative embodiment shown in FIGS. 32-43, the O-ring channel 395 can be eliminated and/or formed at another location.

It will be appreciated and as shown in the cross-sectional views, the lock ring 330 can be formed as a single molded part.

The sample bottle assembly 300 also includes a cap 400. Like the other components described herein, the cap 400 can be formed of any number of different materials, including but not limited to injection moldable plastics and can be formed of a transparent material. The cap 400 has a hollow interior and is defined by a closed first end 402 and an open second end 404. The cap 400 thus has an outer peripheral side wall 410 and an inner wall structure that includes a top wall 412 that closes off the first end 402. Along an outer surface of the outer peripheral side wall 410 at the open second end 404 are outer threads 405. These threads 405 are configured to threadingly mate with the second threads 385 that are part of the lock ring 330.

The inner wall structure can have a serpentine shape that defines a number of annular shaped channels. Part of the serpentine shape of the inner wall structure includes a bottom wall surface 409 that is adjacent an upper hollow space 411 and faces the lock ring 330. The bottom wall surface 409 is positioned such that it engages the O-ring in channel 395 when the cap 400 is securely and threadingly attached to the lock ring 330 so as to provide a seal between the cap 400 and the lock ring 330. In the alternative configuration shown in the figures, the serpentine structure and seal are different.

In use, the cap 400 can be first securely attached to the lock ring 330 by threadingly mating the threads 405, 385 to form a first sample bottle subassembly. In this attached condition, the top of the spire structure 390 is disposed within the upper hollow space 411.

After the cap 400 is attached to the lock ring 330, the first sample bottle subassembly is then securely attached to the sample bottle 310. The threads 340, 370 are configured and formed such that the threads 370 engage the threads 340 prior to engagement between the fins 350 and teeth 320.

In addition, and according to one embodiment, the threads 340, 370 are constructed and the thread time is controlled such that a predetermined number or a partial revolution of the cap 400 results in the cap 400 reaching its thread end and being securely attached to the sample bottle 310. For example, a ⅓ revolution of the cap 400 is used to reach the thread end. During this rotation of the cap 400, the fins compress (flex inward) due to contact with and riding along the swept surfaces 322; however, in order for the fins 350 to flex out and engage the locking surfaces 324 of the teeth 320, a small degree of over rotation beyond the one revolution is required and permitted by design in order to have the fins lockingly engage the teeth.

It will also be appreciated that auditory and tactile feedback are provided to the user in that the user will hear and feel the moment at which the fins 350 flex outward and engage the locking surfaces 324 of the teeth 320. In addition, clear visual confirmation of locking by contact of parts 311, 330 is provided. At this point in time, like a ratchet, the cap 400 cannot be rotated in a direction that results in opening of the cap 400.

As shown in FIG. 25, a lock ring protector 325 can be provided for packaging and transportation of the product prior to use. The lock ring protector 325 can be in the form of a cup shaped cap that is intended for placement over the bottom portion (i.e., the fins 350 and threads 370) of the lock ring 330. The lock ring protector 325 prevents the locking mechanism (fins 350 and teeth 320) from engaging accidentally and protects from contamination.

FIG. 25 also shows at least one unique ID 11 on one or both of the lock ring 330 and the bottle 310. FIG. 25 shows an embodiment in which the ID is provided on the bottle 310. Both IDs must match when two IDs are presented.

Figure 26:
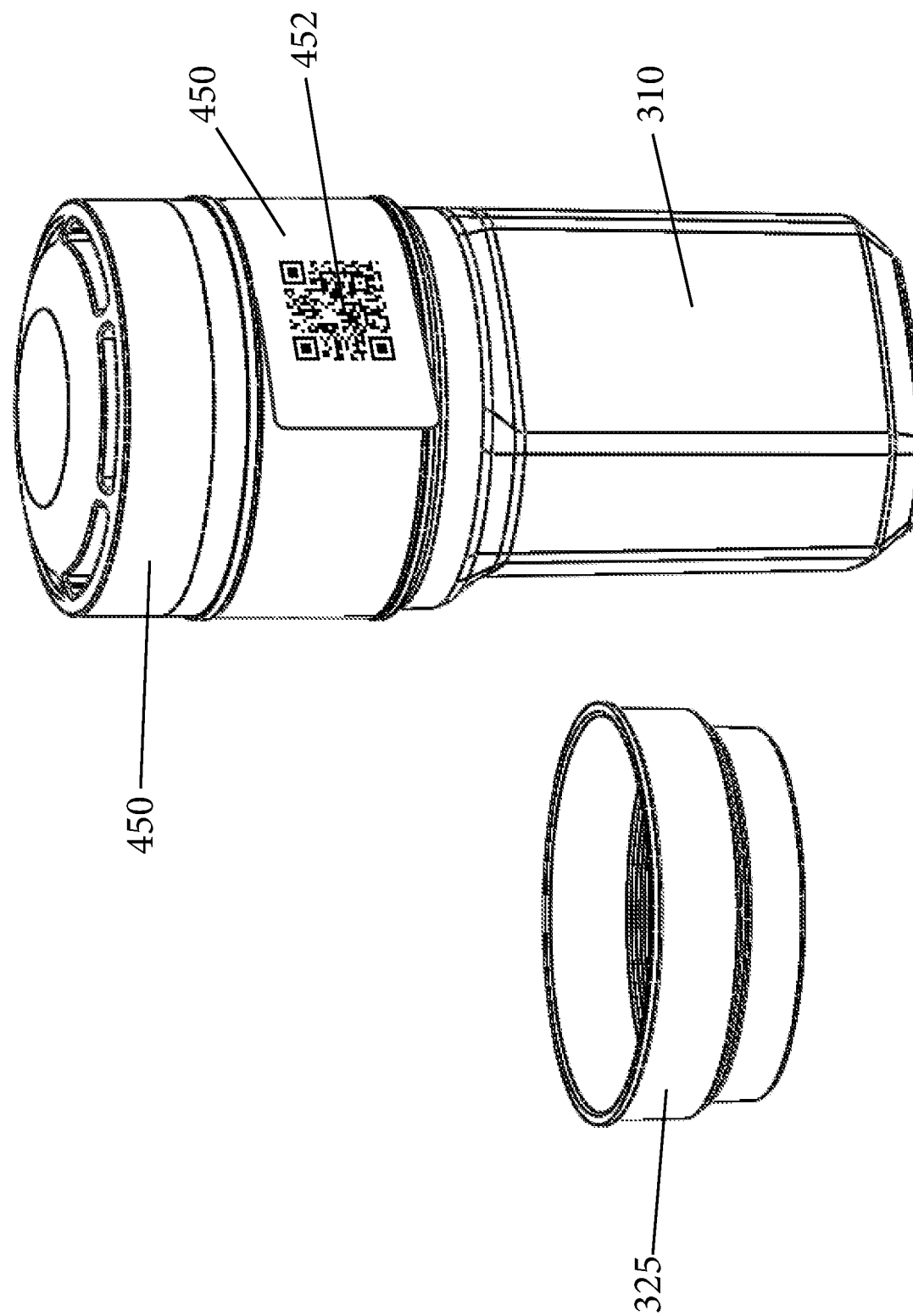
FIG. 26 is an exploded view of the sample bottle assembly with the lock ring protector removed and an opaque security label in place.
Figure 28:
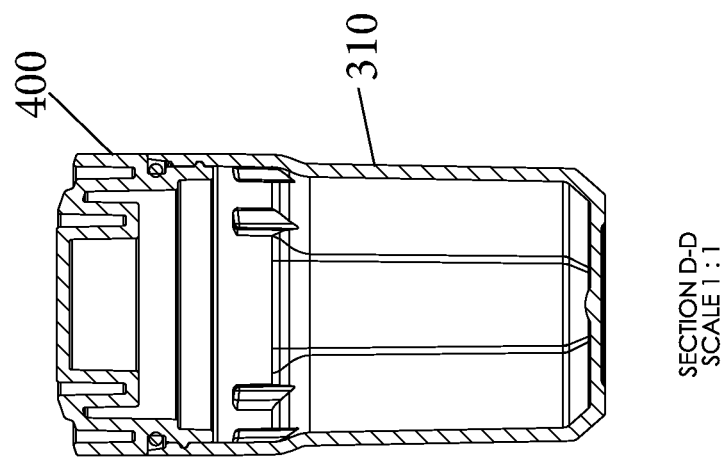
FIG. 28 is a cross-sectional view thereof.
Figure 27:
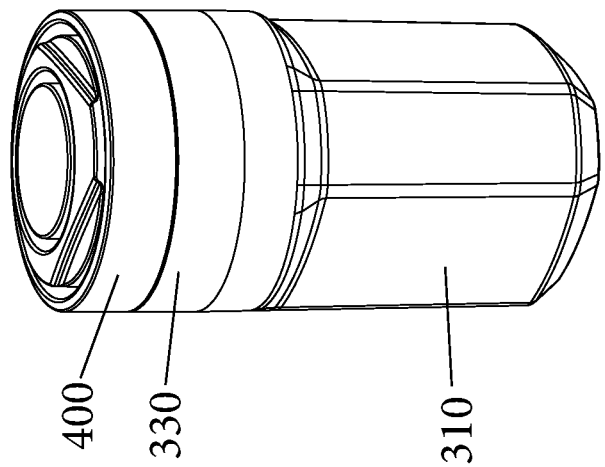
FIG. 27 is a perspective view of the sample bottle assembly in a fully assembled condition.

As shown in FIG. 26, after the sample is provided and unique IDs confirmed and logged into the appropriate records, then an overseeing entity can apply a security label 450 (with or without an optional NFC tag). The label 450 is securely adhered such that it covers the two unique IDs (on the lock ring 330 (FIG. 12) and bottle 310) and also covers the entire circumference of the seam between the lock ring 330 and the bottle 310. The label 450 is opaque so as to prevent viewing of the unique IDs and in this way, an individual at a downstream testing facility cannot locate a particular sample bottle based on the unique ID since it is hidden from view. Identification of the bottle 310 in transit or in the lab is thus prevented by placement of the unique IDs and the placement of the label 450. The illustrated label 450 includes a QR code 452 printed thereon for tracking and identification purposes. It will be appreciated that instead of the QR code 452, a similar machine readable unique ID can be used.

It will be appreciated that the use of security label 450 is optional.

Blood Adaptor Kit

In accordance with another aspect of the present invention, a blood adaptor kit allows for standard blood vials to be securely held inside the sample bottle 310. The blood adaptor kit includes a vial adapter or vial holder. The vial holder comprises an annular shaped structure with a center hole that is defined by a center core (annular shaped wall) and is sized and shaped to receive a traditional blood vial 10. The vial holder includes an outer peripheral side wall that is radially spaced from the center core, with structural ribs connecting the center core to the outer peripheral side wall (annular shaped). A lip can be formed along a bottom edge of the adaptor. The lip can extend circumferentially around the entire bottom edge.

The adaptor can be formed of a molded silicone material.

The blood vial 10 is placed through the center hole of the vial holder and then the adaptor is inserted into the lock ring 330 from the bottom (i.e., it is inserted into center opening thereof). The lip along the bottom edge seats against the core 352 of the lock ring 330. Then the cap 400 and the lock ring 330 as a unit (along with the blood vial 10) are screwed onto the sample bottle 310 until tight. As discussed herein, the molded fins 350 formed as part of the lock ring 330 ratchet over the teeth 320 mechanically preventing the lock ring 330 from unscrewing and blocking access to the locking mechanism in order to resist tampering once closed.

The capped sample bottle 310 can then be placed into temperature controlled transport packaging.

In the assembled position, the top of the blood vial 10 can reach into the hollow interior space of the spire 390.

Figure 31:
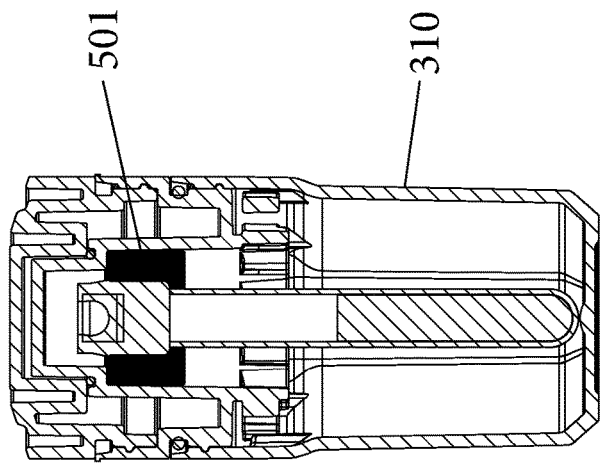
FIG. 31 is a cross-sectional view thereof showing the blood adapter kit in a fully assembled condition.
Figure 30:
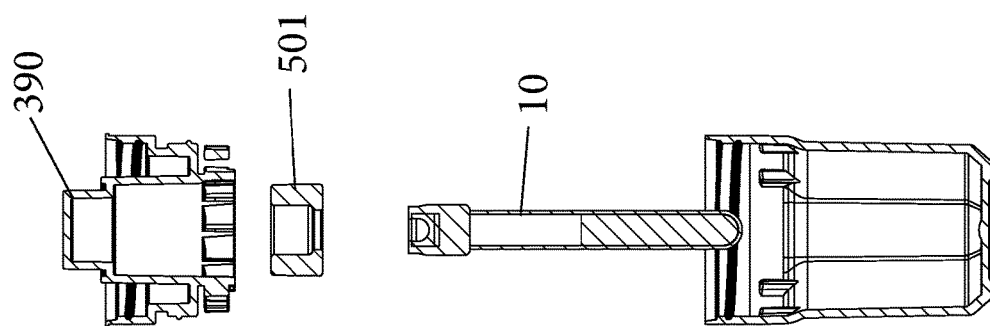
FIG. 30 is a cross-sectional view thereof.
Figure 29:
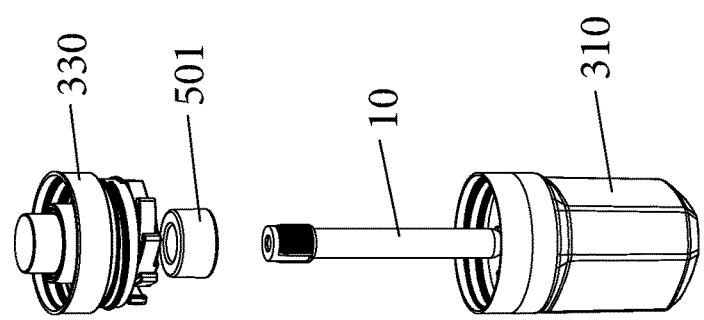
FIG. 29 is an exploded perspective view of another blood adapter kit.

FIGS. 29-31 show another adaptor 501 according to a different embodiment. The adaptor 501 is an annular shaped structure with a center hole through which the vial 10 is inserted. The adaptor 501 is configured to slide along the vial 10 and as shown in FIG. 31, the adaptor 501 is inserted into the hollow interior of the spire 390. The adaptor 501 is positioned within the hollow interior of the spire 390 until the top edge of the adaptor 501 seats against the bottom edge of the inner should formed within the spire 390 where the spire 390 transitions from its wider bottom portion to a narrower top portion.

FIGS. 32-44 set forth another embodiment of the present invention which is similar to the other embodiments and therefore only the difference set forth in this embodiment will be discussed in detail. Unless otherwise noted, the other parts set forth are the same and function in the same manner as described previously.

FIGS. 32-44 illustrate an alternative collection bottle assembly 1000 that is similar to the ones described herein-before and is formed of a number of individual, discrete parts that are assembled to form the sample bottle assembly 1000. The sample bottle assembly 1000 includes a sample bottle 315 and the lock ring 330. The lock ring 330 includes a hollow spire structure 1010 that is similar to the spire structure 390. The spire structure 1010 extends upwardly from the core 352 and protrudes above a top edge of the top section of the outer peripheral side wall 380. The spire structure 1010 can have a variable diameter in that a bottom portion has a larger diameter than a top portion thereof. Alternatively, the spire structure 1010 can have a uniform diameter.

The sample bottle 315 is very to the sample bottle 310 shown in the previous embodiment with the exception that a bottom wall or floor of the sample bottle 315 is contoured as opposed to being substantially flat. In particular, a bottom wall or floor 317 of the sample bottle 315 is contoured in that it is a sloped surface that leads to a center recess 319. The center recess 319 is thus a hole, such as a cylindrical shaped hole.

As shown, the spire structure 1010 includes a side wall 1012 and a top wall 1014 that closes the open end of the spire structure 1010 and extends between the side wall 1012. The side wall 1012 can be tapered toward the top wall 1014. The top wall 1012 can have a contoured outer surface and has a contoured inner surface. In particular, the underside of the top wall 1012 is contoured in that the center portion thereof is raised (e.g., protrusion) with an outer area 1015 outside the raised center portion being smooth.

In the sample bottle assembly 1000, there is a spire insert 1100 that is not present in the previously described samples bottles. The spire insert 1100 is configured to be received within the hollow interior of the spire structure 1010 and more particularly, the spire insert 1100 is intended to be mechanically coupled to the spire structure 1010. For example, a friction fit can be established between the spire insert 1100 and the spire structure 1010 and in particular, the inner diameter at the top of the spire structure 1010 can be slightly less than an outer diameter of the spire insert 1100 and thus, when the spire insert 1100 is inserted into the hollow interior of the spire structure 1010 and is moved toward the top wall 1012, the outer edge of the spire insert 1100 contacts the inner surface of the side wall of the spire structure 1010 resulting in a friction fit. The top end of the spire insert 1100 can contact the underside of the top wall 1012.

The spire insert 1100 can be a hollow cylindrical part and includes one or more protrusions 1115 that protrude outwardly from the outer surface of the side wall of the spire insert 1100. The protrusions 1115 are located at and proximate the open end of the spire insert 1100. There can be a plurality of protrusions 1115 each of which is an annular shaped protrusion that extends around the outer surface of the side wall with the protrusions 1115 being spaced from one another along the length of the of the spire insert 1100. When the spire insert 1100 is inserted into the spire structure 1010, the protrusion 1115 which can be referred to as wipers are in contact with the insert surface of the side wall of the spire structure 1010. The illustrated embodiment can include three wipers 1115.

The wipers 1115 serve to establish a seal between the spire insert 1100 and the inside of the spire structure 1010 and keep the contents from the bottle from coming into contact with the side of the spire insert 1100.

The sample bottle assembly 1000 also includes a cap 1200. Like the other components described herein, the cap 1200 can be formed of any number of different materials, including but not limited to injection moldable plastics and can be formed of a transparent material. The cap 1200 has a hollow interior and is defined by a closed first end 1202 and an open second end 1204. The cap 1200 thus has an outer peripheral side wall 1210 and an inner wall structure that includes a top wall 1212 that closes off the first end 1202. Along an outer surface of the outer peripheral side wall 1210 at the open second end 1204 are outer threads 1205. These threads 1205 are configured to threadingly mate with the second threads 385 that are part of the lock ring 330.

The top wall 1212 includes an inner surface that includes a plurality of locking ribs 1225 that are radially spaced apart from one another. Each locking rib 1225 can have an arcuate shape or be wedge shaped or have other shapes and the locking ribs 1225 can thus be arranged generally in a circle defining a center space that has a complementary shape as the top wall of the spire structure 1010. The locking ribs 1225 are configured to engage the top wall of the of the spire structure 1010 resulting in a press fit (friction fit) between the top of the spire structure 1010 and the cap 1200 to allow reception of the spire structure and establish a friction fit (press fit) to be established between the spire structure 1010 and the cap 1200 when the top wall of the top portion of the spire structure 1010 is press fit into engagement with the locking ribs 1225, thereby coupling the top of the spire structure 1010 to the cap 1200.

Between the outer peripheral side wall 1210 and the inner wall structure, there can be an annular shaped groove or spaced arcuate channels 1215.

Figure 38:
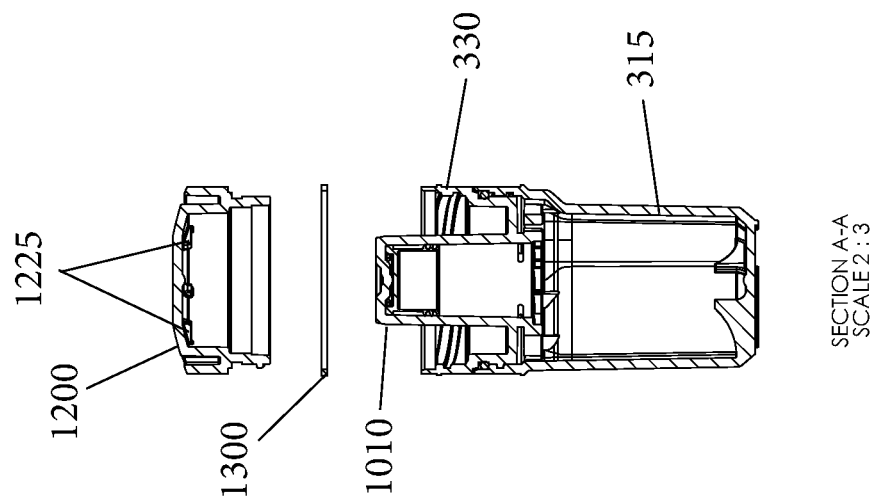
FIG. 38 is a cross-sectional view thereof.
Figure 37:
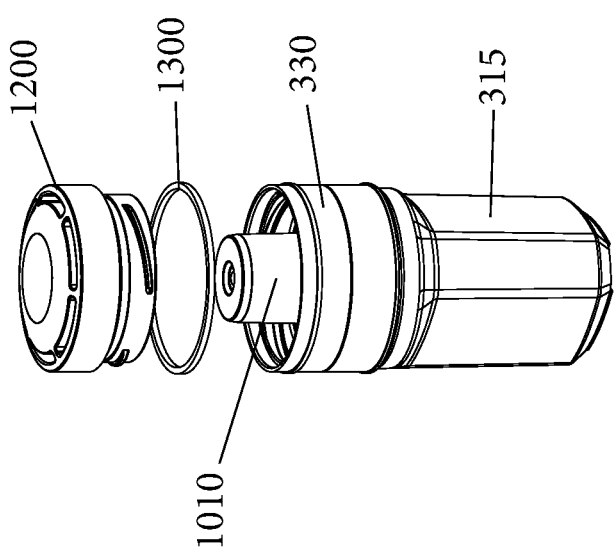
FIG. 37 is an exploded perspective view showing the collection bottle assembly in a partially assembled condition in which the cap and cap spacer have been removed.

As shown in FIGS. 37-38, a cap spacer 1300 can be provided and as described herein, the cap spacer 1300 functions to prevent engagement of the cap 1200 to the spire structure 1010 and more particularly, prevents the top of the spire structure 1010 from being press fit into engagement with the underside of the cap 1200 and thus prevents the attachment of the two. The cap spacer 1300 is merely a ring-shaped structure that has a selected thickness such that when the cap 1200 threadingly mates with the lock ring, the top of spire structure 1010 does not contact and engage the locking ribs 1225 but instead remains positioned therebelow as shown in sheet 26.

Figure 35:
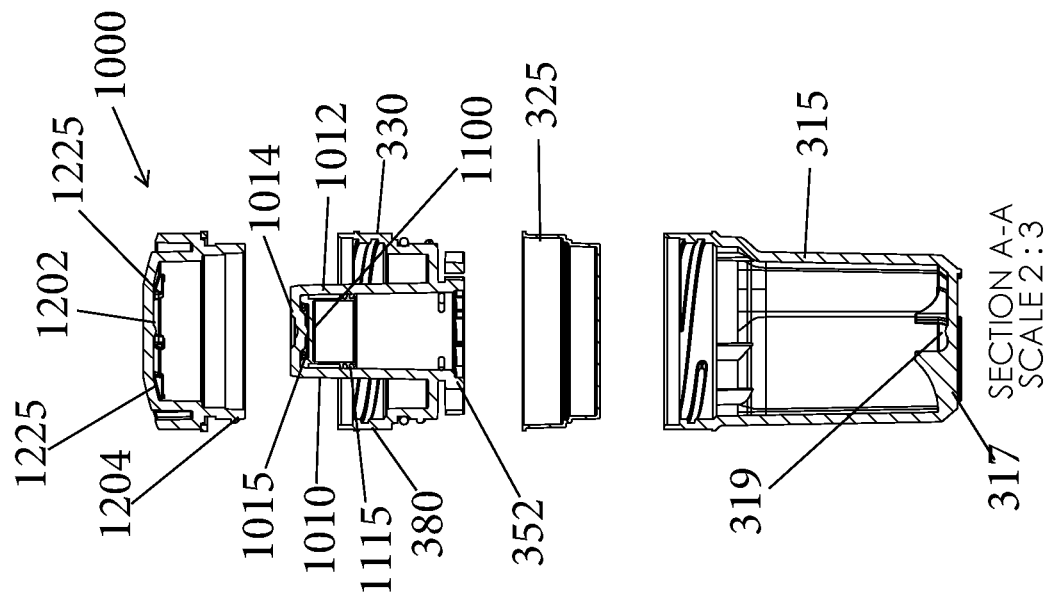
FIG. 35 is a cross-sectional view thereof.
Figure 34:
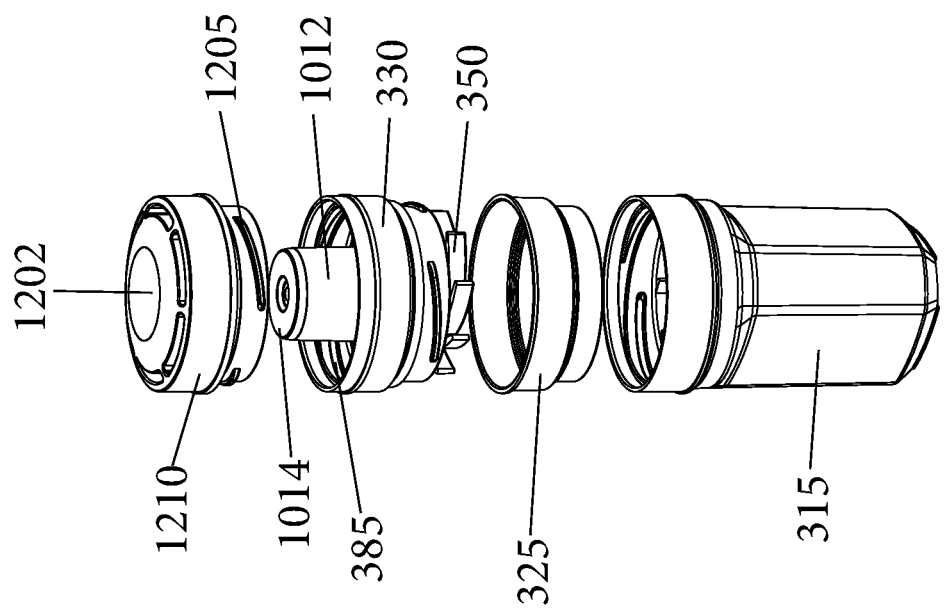
FIG. 34 is an exploded perspective view of the collection bottle assembly prior to assembly.

FIGS. 34-35 are exploded views showing the various parts of the sample collection bottle 1000. The lock ring protector 325 is shown and functions in the manner described herein previously. The spire insert 1100 is shown engaged with the interior of the spire structure 1010 and more particularly, the spire insert 1100 is shown press fit to the underside of the spire structure 1010. As discussed previously, the outer diameter of the spire insert 1100 is slightly greater than an inner diameter of the side wall of the spire structure 1010 at least at a top portion thereof and thus, when inserted into the hollow interior of the hollow spire structure 1010 and driven toward the top wall of the spire structure 1010, a press fit is formed between the spire insert 1100 and the spire structure 1010.

Figure 36:
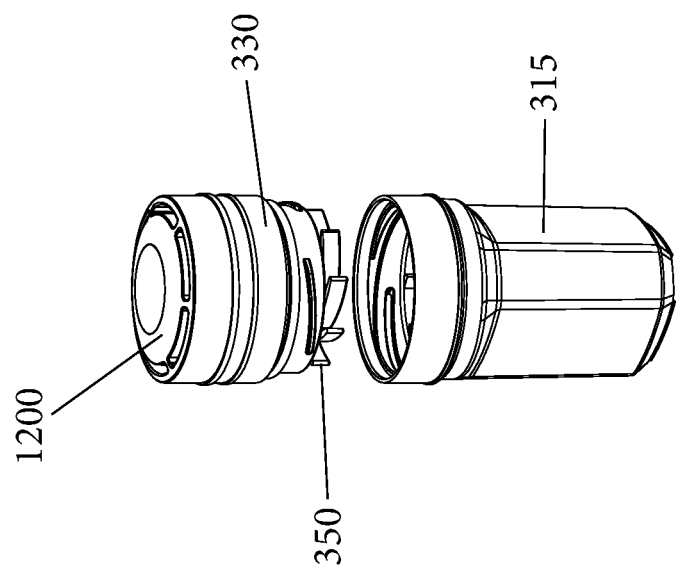
FIG. 36 is an exploded perspective view showing the collection bottle assembly in a partially assembled condition in which a cap, with cap spacer, is coupled to a lock ring.

FIG. 36 shows the cap 1200, with cap spacer 1300, coupled to the lock ring 330. The base 315 is separated therefrom and can receive sample. The assembled cap 1200, cap spacer 1300 and lock ring 330 can be referred to as being an assembled cap.

FIG. 33 shows the assembled cap attached to the base 310 as by threadingly attaching the lock ring 330 to the base 315. The cap spacer 1300 is shown and the presence of the cap spacer 1300 prevents attachment between the spire structure 1010 and the cap 1200. In this position, the sample is securely contained in the base 315 due to the secure connection between the lock ring 330 and the base 315.

FIGS. 37-38 show removal of the cap 1200 and the cap spacer 1300. It will be appreciated that, as shown, a top portion of the spire structure 1010 is exposed and accessible since it is positioned above the top edge of the lock ring 330.

Figure 39:
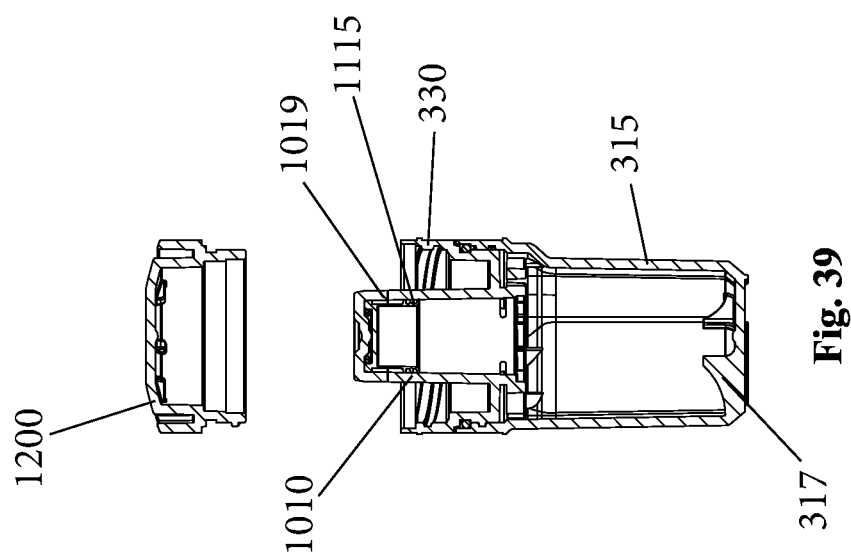
FIG. 39 is a cross-sectional view thereof showing a spire structure cut at a predetermined location.

Next, FIG. 39 shows the spire structure 1010 being cut at a location about the top edge of the lock ring 330 (a cut line 1019 is shown to represent the cut location which separates the top portion of the spire structure from the bottom). Any number of different cutting processes can be utilized so long as the controlled cut only results in the spire structure 1010 being cut and not the spire insert 1100 being cut. The wipers 1115 of the spire insert 1100 serve to protect the collected sample from being contaminated since the flexible wipers seat and seal against the inner surface of the side wall of the spire structure 1010 at a location that is below the cut location. Thus, contaminants cannot pass by the spire insert 1100 to the collected sample in the base 315. The wipers 1115 thus act as sealing elements.

The result of this cutting operation is that the spire structure 1010 now has a top cut portion that can be removed from the bottom portion of the spire structure 1010 which remains fixedly attached to the base 310.

Figure 40:
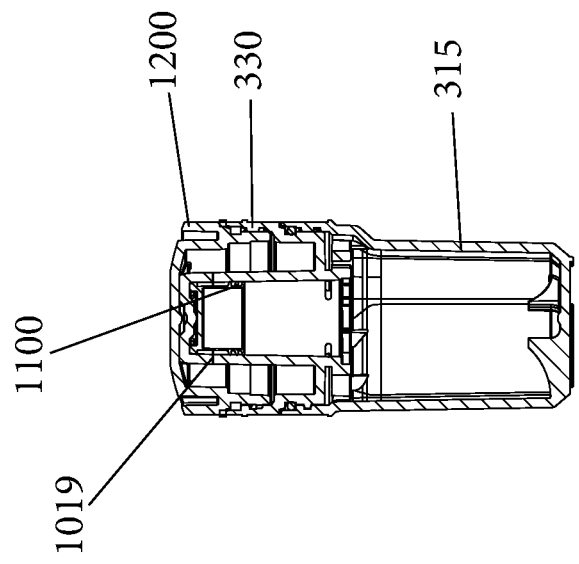
FIG. 40 is a cross-sectional view thereof showing the cap screwed back onto the lock ring with the cap spacer removed.

Next, as shown in FIG. 40, the cap 1200 is screwed back into engagement with the lock ring 330 and since the cap spacer 1300 has been removed, when the cap 1200 is fully threaded onto the lock ring 330, the cut top portion of the spire structure 1010 can freely engage the underside of the cap 1200. This results in a press fit being established between the cut top spire portion and the cap 1200 and thus, the two are attached to one another.

Figure 41:
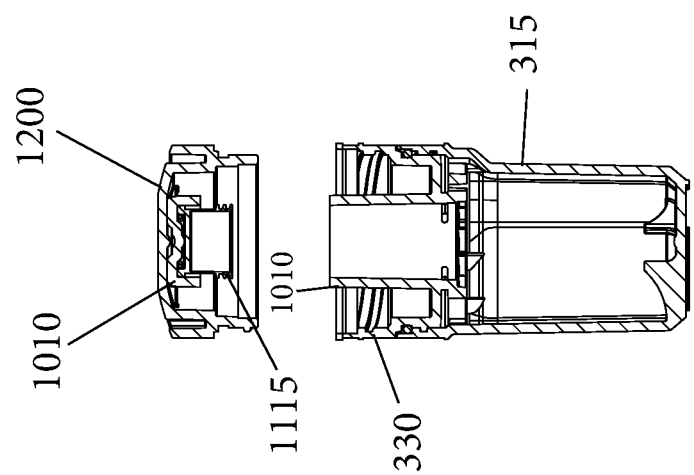
FIG. 41 is an exploded cross-sectional view showing removal of the cap from the lock ring.

FIG. 41 shows the removal of the cap 1200 from the lock ring 330 as by unscrewing the cap 1200 from the lock ring 330. Since the top spire portion has been cut and it attached to the cap 1200, the removal of the cap 120 results in the cut top spire portion separating from the intact bottom spire portion. As shown in FIG. 41, with the removal of the cut top portion, the spire structure 1010 can be freely accessed and is open to allow direct access to the sample stored in the base 315.

It will be appreciated that in an alternative embodiment, the lock ring 330 can be eliminated and instead, the outer threads 1205 are configured to threadingly mate with the internal threads 340 that are part of the collection bottle 310.

Blood Vial Storage

Figure 43:
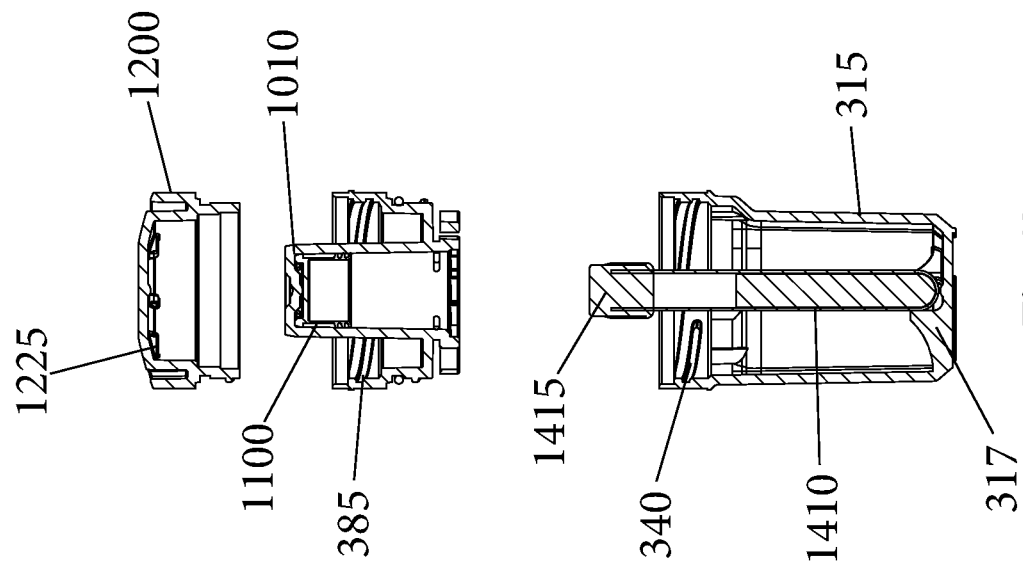
FIG. 43 is an exploded cross-sectional view thereof.
Figure 42:
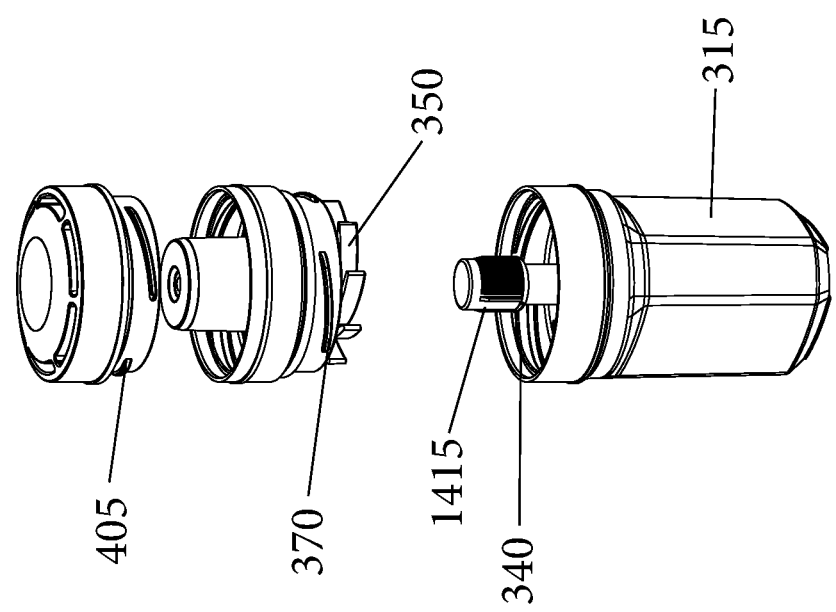
FIG. 42 is an exploded perspective view of the collection bottle assembly configured for blood vial storage.
Figure 47:
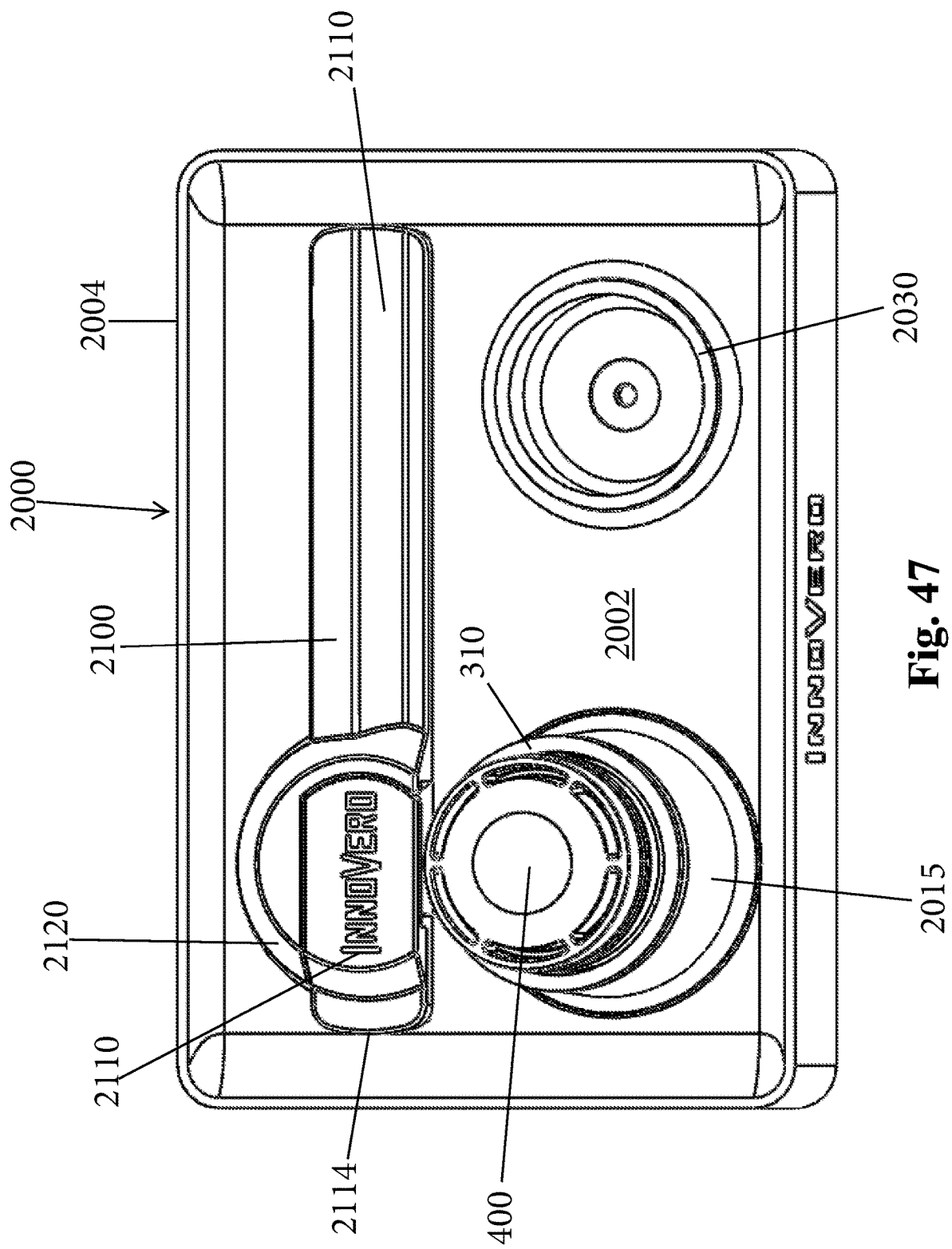
FIGS. 47-60 illustrate a lab opener bench-top rack and a lab opener assembly for opening the collection sample bottle.

FIGS. 42-44 illustrate another aspect of the present invention and in particular, these sheets show the use of the sample bottle assembly 1000 as a means for storing a blood vial 1400 in a secure upright position.

It will be appreciated that the spire structure 1010 is intact and has not been cut yet.

The blood vial 1400 includes a blood collection tube 1410 that has an open top end and a closed bottom end. Traditional, blood collection tubes 1410 have cylindrical shapes. The blood vial 1400 also includes a stopper 1415 that sealingly closes off the open top but is easily removable therefrom. The stopper 1415 is traditionally formed of a rubber material or similar material; however, other materials can be used. In addition, and as illustrated, the stopper 1415 can have a slot (annular shaped) into which the top edge of the blood collection tube 1410 is received, thereby sealing the blood collection tube 1410.

In order to assist in locating and holding the blood collection tube 1410, the closed bottom end of the blood collection tube 1410 is disposed within the center recess 319. Since the sloped floor 317 surround a bottom portion of the blood collection tube 1410, the blood collection 1410 is maintained in vertical position (e.g., parallel to the side wall of the sample bottle 315. This locating feature also assists in preventing any undesired movement of the blood vial 1400 during transportation or other movement of the sample bottle assembly 1000.

The top of the blood vial 1400 is held in place by the spire insert 1100 and in particular, the top of the blood vial 1400 is received within the hollow interior of the spire insert 1100. The spire insert 1100 thus surrounds the top of the blood vial 1400 and in particular, surrounds the stopper 1415 The sample bottle 315 is very similar to the sample bottle 310 shown in the previous embodiment with the exception that a bottom wall or floor of the sample bottle 315 is contoured as opposed to being substantially flat. In particular, a bottom wall or floor 317 of the sample bottle 315 is contoured in that it is a sloped surface that leads to a center recess 319. The center recess 319 is thus a hole, such as a cylindrical shaped hole. Since the bottom and top of the blood vial 1400 are held in place, the blood vial is secured in a fluid collection environment offering the benefits described herein.

FIG. 44 shows the blood vial 1400 held in place but due to the presence of the cap spacer 1300, the cap 1200 is not fully secured to the lock ring 330 as described herein and the spire structure 1010 is not engaged to the cap 1200.

FIGS. 42-43 are exploded views in which the cap 1200 is removed from and not engaged to the spire structure 1010 of the lock ring. The spire insert 1100 is shown as being securely held within the interior of the spire structure 1010 as described previously. The blood vial 1400 is held along the floor of the sample bottle 315.

Once the blood sample is disposed within the collection bottle, the lock ring locks in place with the sample bottle 315 in the manner described hereinbefore. The blood vial 1400 is thus securely held below the spire structure 1010 and within the sample bottle 315. To access the blood sample, the cap 1200 is removed and the cap spacer 1300 is removed and a cutting operation is performed using any number of techniques, such as those described herein. For example, a cutting device can be used to cut through only the spire structure 1010 while leaving the spire insert 1100 intact. The cap 1200 is then screwed onto the lock ring and, as described herein, the cut top portion of the spire structure 1010 is coupled to the underside of the cap 1200 and since the spire insert 1100 is coupled to the spire structure 1010, the removal of the cap 1200 results in removal of both the cut top portion of the spire structure 1010 and the spire insert 1100 that is held therein. This results in the stopper 1410 being exposed and accessible. The stopper 1410 can be removed in order to access the fluid (blood) that is within the blood vial 1400. Alternatively, the stopper 1410 can be eliminated and the septum can be pierced in order to remove blood.

The cap 1200 can then be reattached by screwing the cap 1200 back onto the lock ring.

In this manner, the blood vial 1400 is securely held in place during the collection process and during transportation of the blood vial.

It will be appreciated that in the embodiments shown in FIGS. 32-44, the lock ring 330 serves the same purpose in that it provides a unique mechanism/technique for ensuring that the collected sample, whether it is a blood sample or urine sample, is in a tamper proof environment.

Lab Intake

Once the secured sample bottle 310 arrives at a test facility (lab), the sample bottle 310 is ready for processing and testing/analysis of its contents. In one embodiment, the processing of the bottle 310 can occur at a station or device that is constructed to perform one or more functions described below. In particular, at the lab intake station, the sample bottle 310 is opened to allow access to the contents. The opening of the bottle 310 can occur by removing the cap 400 from the lock ring 330. The optional security label 450 (FIG. 26) covers the seam between the bottle 310 and the lock ring 330. In the event that an athlete or the like requests that the unique IDs be reviewed, the security label 450 can be removed and the unique IDs can be compared to confirm they are the same. The identification of the bottle 310 can be logged since the unique IDs are now visible due to removal of the security label. The identification process can occur by any number of different means and techniques, including using an automated reader or can even be performed manually. Part of one exemplary identification process can be to confirm that the two unique IDs match one another.

The opening of the bottle 310 can be performed by removing the top portion of the spire 390. The spire 390 can be formed with a weakened portion (break line) to assist in removal of the top portion. The removal can be either done manually, as by using a special tool (e.g., a wrench) that engages and twists the spire's top portion until it cleanly breaks off or it can be done in an automated manner using a cutting device. Any number of different types of cutting devices are available for performing such task including but not limited to a fixed blade cutter, a hot wire cutter, rotary cutter, die punch, iris/guillotine cutter, impact socket, etc. The cutting operation can thus be a manual process in which a user uses a tool to perform the cut or can be an automated process performed by an automated device.

It will therefore be understood that an opener intended for use in the present invention comprises a device that is capable of cutting and separating a top portion of the spire structure from the bottom portion of the spire structure. Any number of different techniques can be used to accomplish this task including mechanical devices, like blades, to optical equipment, such as a laser, etc. In yet another embodiment, the spire structure can have a weakened portion, such as a circumferential line that generally partitions the spire structure into the top portion and the bottom portion. When a force is applied to the spire structure, such as by a jaw or clamp, the spire structure breaks along the weakened portion and the top portion can be separated and removed.

In yet another aspect, the lab intake station can include an optical inspection feature. For example, the optical inspection can include recording 3D video under multiple light sources (IR, visible, UV) to create a digital record for future reference/forensics.

Yet another optional feature that can be incorporated into the lab intake station is an automated aliquot feature in which an aliquot can be taken from the liquid sample contained in the sample bottle 310. This can be done in an automated manner using a robotic device or the like in which a pipette or the like is inserted into the top opening formed in the spire 390 into contact with the liquid sample which is then drawn into the pipette for aliquoting and/or testing.

Lab Opener

FIGS. 47-60 illustrate a lab opener bench-top rack 2000 and a lab opener assembly 2100 for opening the sample bottle 310.

The bench-top rack 2000 comprises a substrate that can, in one embodiment, be supported by a support surface, such as a lab bench (not shown). Any number of techniques can be used to mount (detachably or fixedly) the bench-top rack 2000 to the support surface. In the illustrated embodiment, the bench-top rack 2000 can be in the form of a tray that has a floor 2002 with an upstanding peripheral side wall 2004. The bench-top rack 2000 includes a first recessed section 2010 (FIG. 50) for receiving and holding the lab opener assembly 2100 within the bench-top rack 2000; a first raised portion 2015 (e.g., cup shaped receptacle) for holding the sample bottle assembly 300; and a second raised portion 2030 (e.g., cup shaped receptacle) for holding the cap 400.

The first raised portion 2015 is in the form of a hollow upstanding structure and more particularly, is defined by a first annular shaped wall. The first raised portion 2015 thus extends upwardly from the floor 2002 and an inner footprint thereof is complementary to the shape of the sample bottle 310. More specifically, the hollow interior of the first raised portion 2015 has a complementary shape of the sample bottle 310. At least a bottom portion of the sample bottle 310 has a non-circular shape and thus, the sample bottle 310 is not capable of rotating within the hollow interior of the first raised portion 2015. The first raised portion 2015 is designed to locate and hold the sample bottle 310 in place along the bench-top rack 2000 to permit a cutting operation to be performed as described below. While the interior of the first raised portion 2015 has a non-circular shape, the outer surface of the first raised portion 2015 can have a circular and shape.

The height of the first raised portion 2015 is selected such that the sample bottle 310 is mostly contained within the first raised portion 2015; however, a top end of the lock ring 330 is located above the top edge of the first raised portion 2015.

Figure 53:
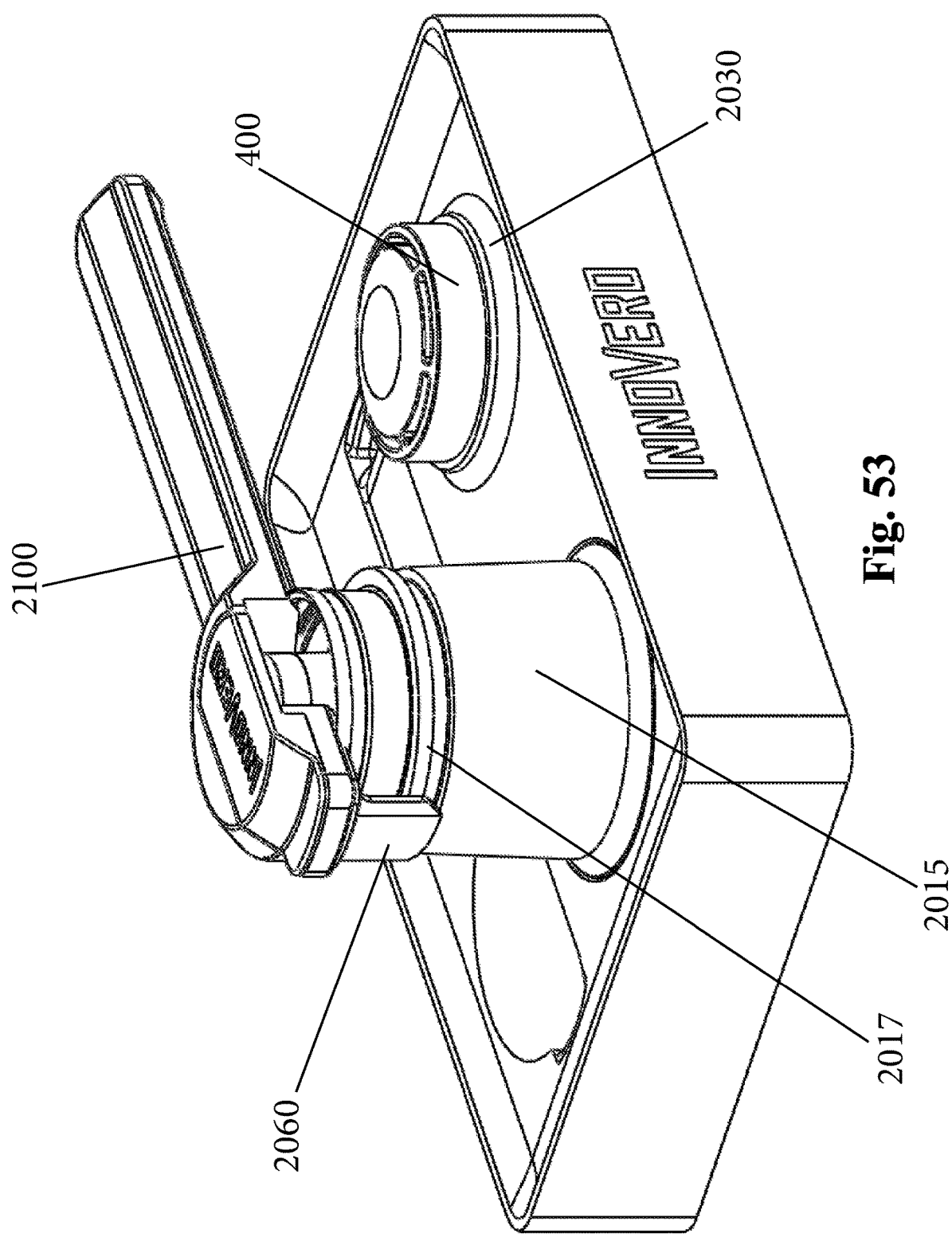

As best shown in FIG. 53, the first raised portion 2015 has a continuous outer groove 2017 formed along an outer surface thereof. The outer groove 2017 is formed at or proximate a free top end 2019 of the first raised portion 2015.

Figure 49:
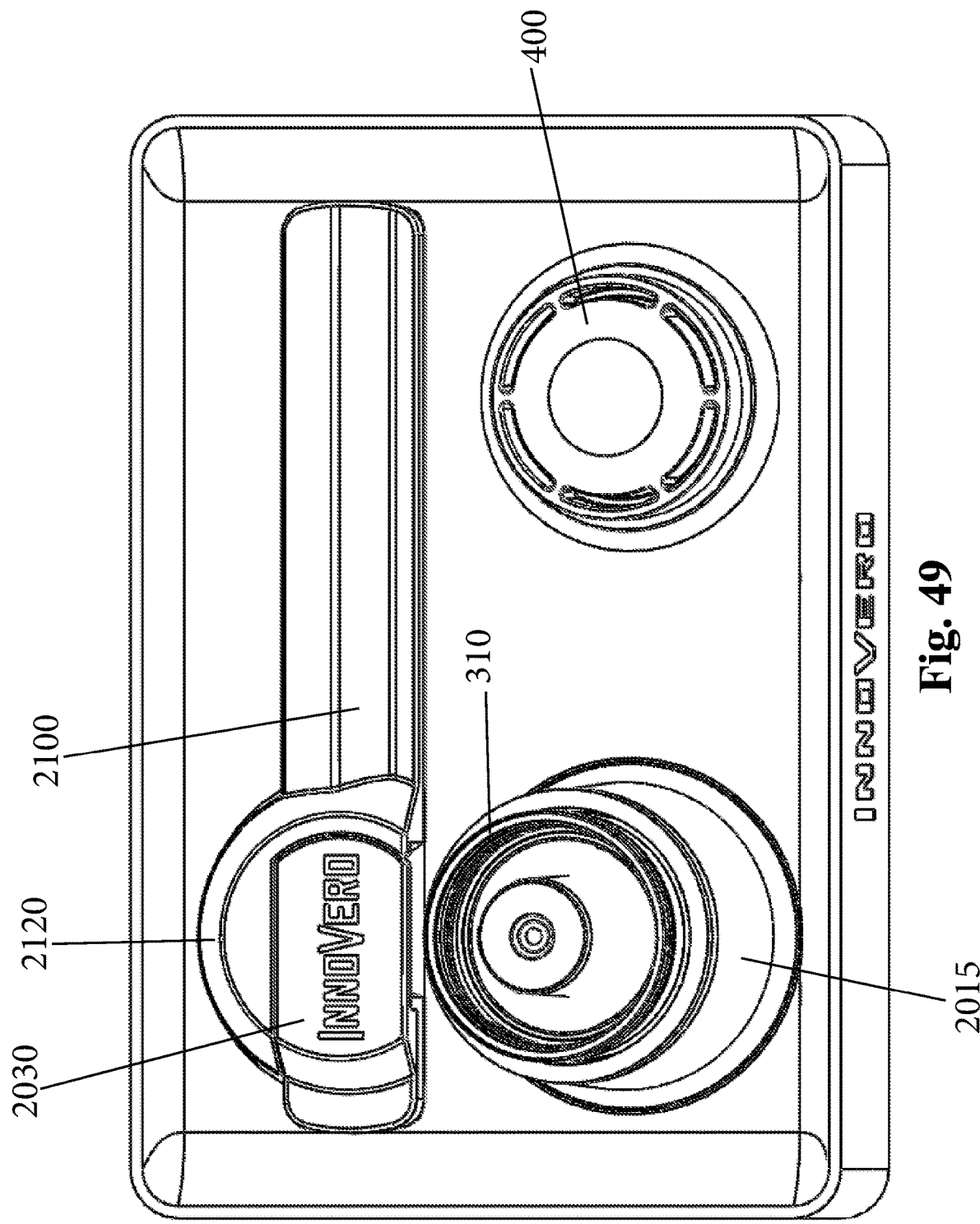
Figure 50:
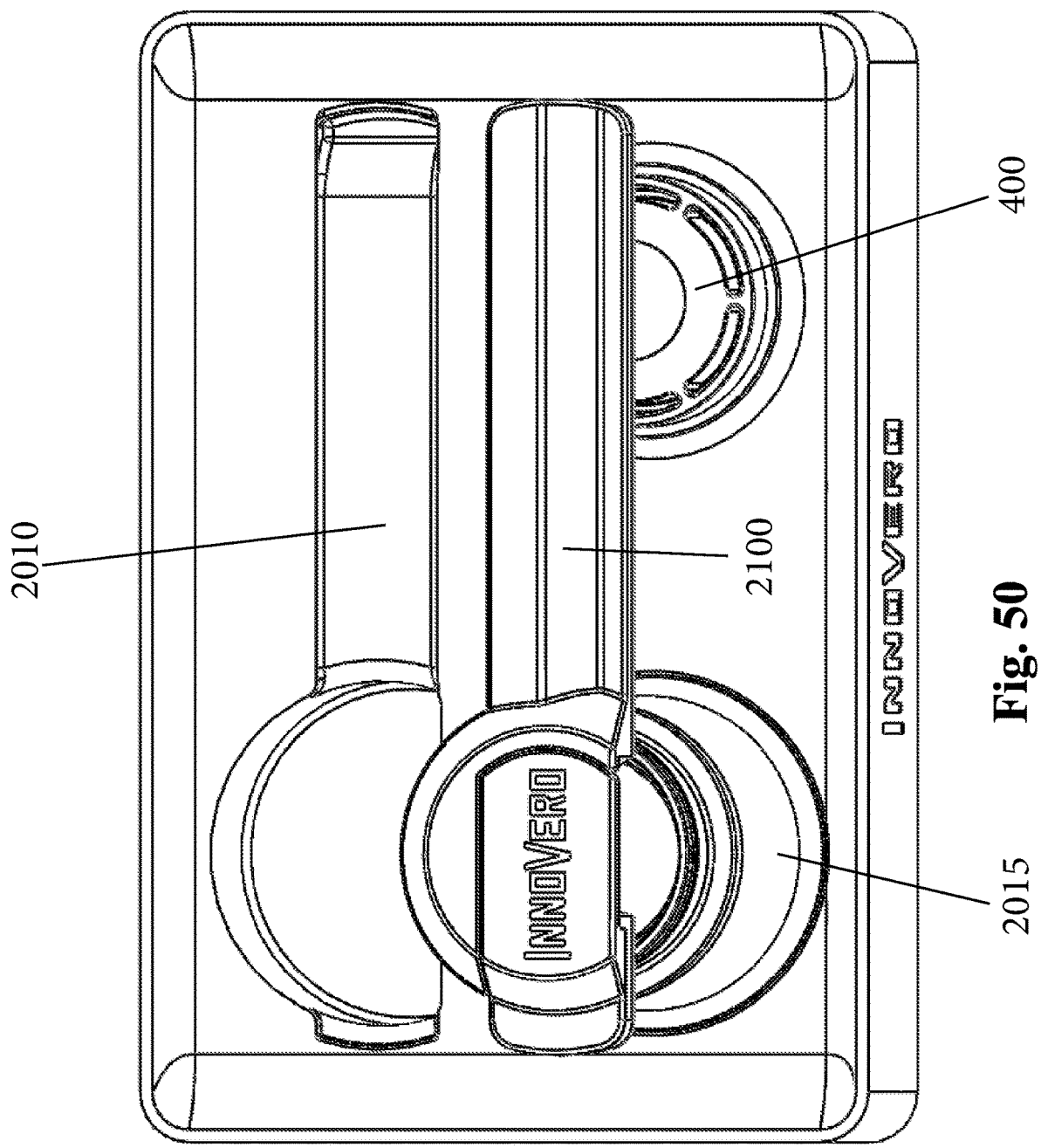

The second raised portion 2030 for holding the cap 400 is also in the form of a hollow upstanding structure that has a hollow interior that is configured to receive and hold the cap 400. Since the cap 400 has a circular shape, the hollow interior of the second raised portion 2030 is circular shaped. Thus, both the inner and outer surface of the second raised portion 2030 can be circular in shape. FIG. 49 shows the cap 400 disposed within the hollow interior of the second raised portion 2030.

The height of the second raised portion 2030 is less than a height of the first raised portion 2015 since the second raised portion 2030 only holds the cap 400. The height of the second raised portion 2030 can be selected such that at least a top portion of the cap 400 extends above the top edge of the second raised portion 2030 to allow the cap 400 to be grasped and removed from the second raised portion 2030. Additionally, it is designed such that no part of the raised portion 2030 or the rack 2000 contacts the inside of the cap 400 to reduce the potential for contamination.

The bench-top rack 2000 and the features described herein are preferably formed as a single integral structure, such as a single molded structure.

As mentioned, the bench-top rack 2000 can be mounted to the support surface using any number of traditional techniques, including but not limited to the use of fasteners, clamps, etc.

Lab Opener Assembly (Spire Cutter)

The lab opener assembly 2100 is configured to open the sample bottle assembly 300 and in particular and according to one exemplary embodiment, the lab openers assembly 2100 is in the form of a spire cutter. The spire cutter 2100 is of a manual type and is intended, as described herein, to be grasped by the user and positioned about the spire structure and then operated to cut the spire structure.

The spire cutter 2100 includes a handle 2110 that has a first end 2112 and an opposing second end 2114. The handle 2110 is an elongated structure and the user grasps the handle 2112 proximate the first end 2112. At or proximate the opposing second end 2114, the handle 2110 has a curved shaped and in particular, the body of the handle 2110 at the second end 2114 is defined by a curved wall 2120 with an opening or space 2115 being defined between the ends of the curved wall 2120. As illustrated, the curved wall 2120 can be generally C-shaped and the opening 2115 can have a hemispherical shape and more particularly, the opening 2115 is sized and shaped to receive the spire structure 1010. More specifically, the spire structure 1010 is intended to be nested within the curved wall 2120.

A distal portion of the curved wall 2120 has a hollow space 2122 and in addition, the curved wall 2120 along its inner surface has a slot or opening 2124 that leads into the hollow space 2122.

Figure 48:
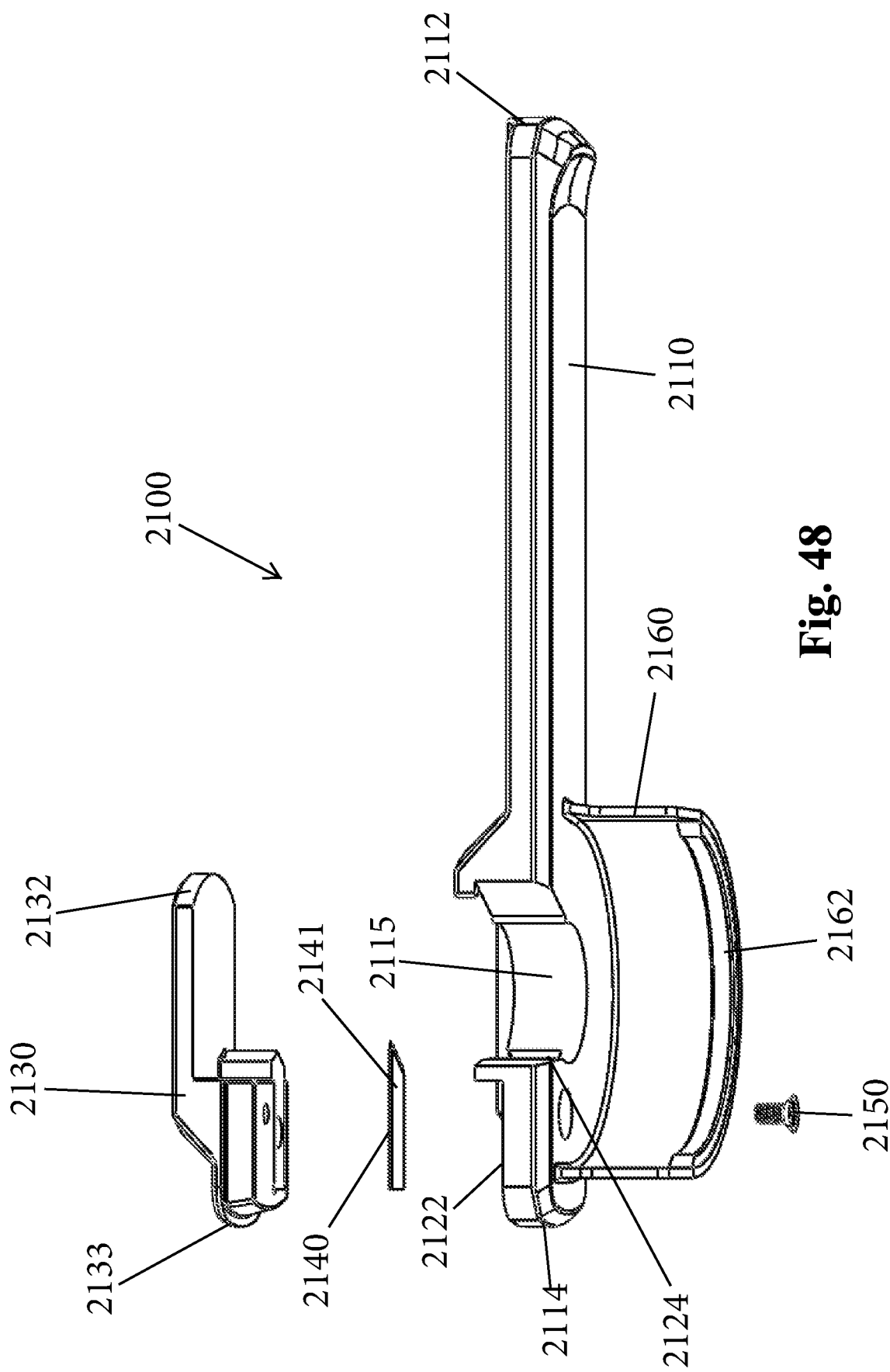

The spire cutter 2100 also has a cover 2130 that closes off the hollow space 2122. The cover 2130 has a curved outer edge 2133 and along an inner edge 2032. As best shown in FIG. 48, the cover 2130 can have a stepped construction. An inner portion of the cover 2130 extends over the opening 2115 and thus, serves to cover said opening. As shown in Sheet 38 the top surface of the handle 2110 can have a raised flange that extends around the opening 2115 (the flange can have an arcuate shape) with the slot 2124 passing through the flange so as to form an entrance (passage) into the opening 2115. When the cover 2130 is disposed on the handle 2110, the thicker outer end 2133 of the cover 2130 is disposed on and secured to the second end portion of the handle 2110 and the shoulder of the cover 2130 defined by its stepped shape seats against the flange. The cover 2130 is secured to the body of the handle 2110 using conventional techniques, such as use of one or more fasteners 2150 (e.g., in the illustrated embodiment, a screw 2150 or the like is used).

A cutting element 2140 is disposed within the hollow space 2122 and in particular, the cutting element 2140 is anchored within the hollow space 2122 (between the cover 2130 and the handle body 2110). For example, the cutting element 2140 can be secured within the hollow space 2122 using any number of traditional techniques. The cutting element 2140 can be in the form of a fixed metal blade or the like. The cutting element 2140 can be disposed within a contoured recess formed in the floor of the hollow space 2122 (the recess can thus serve as a locating feature) or the cutting element 2140 is disposed along a surface of the handle body and then is secured when the cover 2130 is fastened (in one embodiment, the fastener 2150 can pass through the cutting element to locate and secure it). One end 2141 of the cutting element 2140 constitutes a sharp cutting edge that is disposed within the slot 2124 of the curved wall 2120. More specifically, the sharp cutting edge 2141 at least partially extends within the opening 2115 so as to allow the sharp cutting edge 2141 to be placed into contact with the spire structure 1010 and in particular, the sharp cutting edge 2141 is constructed to pierce the spire structure 1010.

The spire cutter 2100 also has a downwardly depending flange 2160 that extends downwardly from the handle 2110. As shown in FIG. 48, the flange 2160 has an arcuate shape and is formed around the opening 2115. For example, the flange 2160 can be generally C-shaped. The flange 2160 has an inner surface with a raised rail 2162 being formed along the inner surface. The rail 2162 is located at or proximate the exposed bottom edge of the flange 2160. The rail 2162 is sized and shaped in view of the shape and size of the groove 2117 of the first raised portion 2115 since the rail 2162 is received within the groove 2117 as a means for coupling the spire cutter 2100 to the sample bottle assembly 300 and limiting the vertical movement of the spire cutter 2100 during the cutting operation. In other words, by fixing the rail 2162 within groove 2117, the spire cutter 2100 is only permitted to rotate about the sample bottle assembly 300 and is not permitted to move or waiver along the vertical axis, thereby ensuring that a level (horizontal) cut is made (perpendicular to the plane of rotation).

The spire cutter 2100 operates by inserting the top portion of the spire structure 1010 into the opening 2115 defined by the curved wall 2120. The sharp cutting edge 2141 pierces the spire structure 1010 but not the spire insert 1100. The handle 2110 is grasped and is rotated about the spire structure 1010 so as to cause the sharp cutting edge 2141 to travel completely around the spire structure 1010 resulting in a complete cutting of the top portion of the spire structure 1010 as described herein. It will be appreciated that the cutting action results from relative movement (rotation) between the sample bottle assembly and the spire cutter 2100. For example, the spire cutter 2100 can be rotated relative to the sample bottle assembly or alternatively, the spire cutter 2100 after it pierces the spire structure 1010 can be held stationary and the sample bottle assembly 300 itself can be rotated much like a traditional motorized can opener.

The degree of which the sharp cutting edge 2141 protrudes from the inner wall (surrounding opening 2115) is selected in view of the thickness of the spire structure 1010. More specifically, the sharp cutting edge 2141 can pierce and extend completely through the spire structure 1010 but not contact and pierce the spire insert 1100. Thus, when the spire structure is fully inserted into the cutter, the sharp cutting edge 2141 pierces the wall of the spire structure 1010 but does not pierce the spire insert 1100 and the curved outer surface of the spire structure 1010 seats against the inner surface of the curved wall 2120. As discussed herein, with the spire structure 1010 remaining stationary, the spire cutter 2100 is then rotated about the spire structure resulting in a clean cut through the spire structure 1010.

The cover 2130 can be removed to allow access to the cutting element 2140 for replacing of the cutting element 2140 when needed or to perform other maintenance or the like.

The spire cutter 2100 can be thought of as being a fixed blade pierce cutter.

As shown in FIG. 49, during the intake, the lab tech inspects the box and removes the box security label, removes and inspects the security bags, then removes and inspects the sample bottle assemblies (sample bottles) 300. The lab tech inserts the bottle (base 310) into the first raised portion 2015 which snugly holds the base 310 of the sample bottle assembly 300. Given the irregular shape of the base 310 of the sample bottle assembly 300, the base 310 does not freely rotate within the first raised portion 2015.

As shown in FIG. 49, the access the sample, the lab tech removes the cap 400 and the cap spacer from the sample bottle assembly 300 to expose the spire structure 1010 and the cap spacer 1300 is discarded.

The cap 400 is placed within the second raised portion 2030. The lab opener 210 is removed from the first recessed portion.

Figure 51:
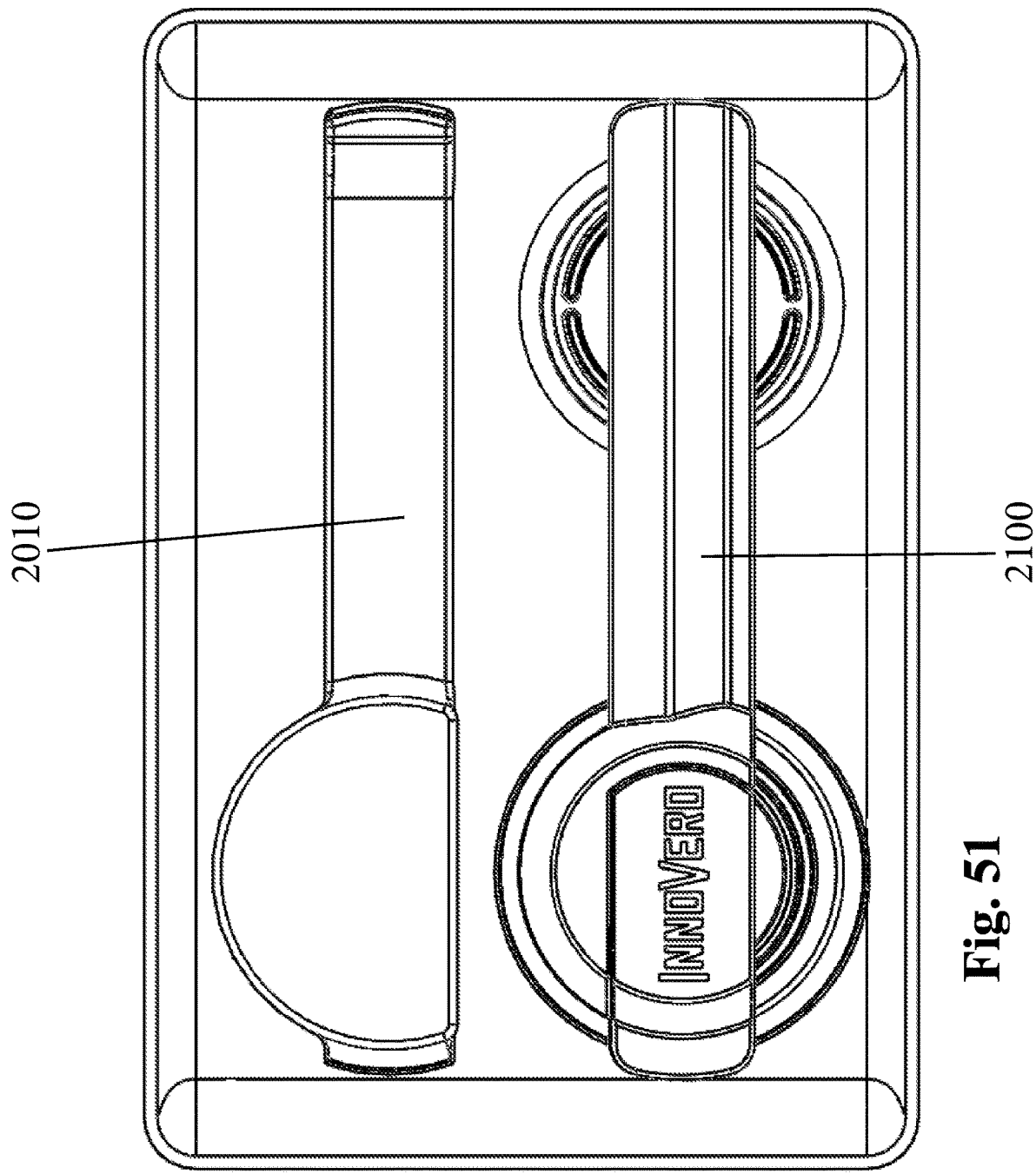

As shown in FIG. 51, with the spire structure 1010 exposed, the lab tech engages the spire cutter 2100 and the spire cutter 2100 is disposed about the spire structure 1010. The handle 2110 is pivoted to pierce the spire structure 1010 with the blade 2140.

In accordance with the present invention and as described above, when the spire cutter 2100 engages the sample bottle assembly 300, the spire cutter 2100 is positioned with its rail 2162 contained within groove 2017 of the first raised portion 2115 to restrict and prevent vertical movement of the spire cutter 2100 during the cutting operation.

It will also be appreciated that the cover 2130 also covers the sharp edge 2141 so as to act as a safety feature and prevent the lab tech from coming into contact with the sharp blade 2141. In addition, the cover 2130 also serves to prevent any undesired movement of the cut spire structure 1010 as described herein since the cover 2130 covers and is located above the spire structure 1010 and thus, if the spire structure 1010 is ejected upon completing the cutting, the cover 2130 contains the spire structure 1010.

Figure 52:
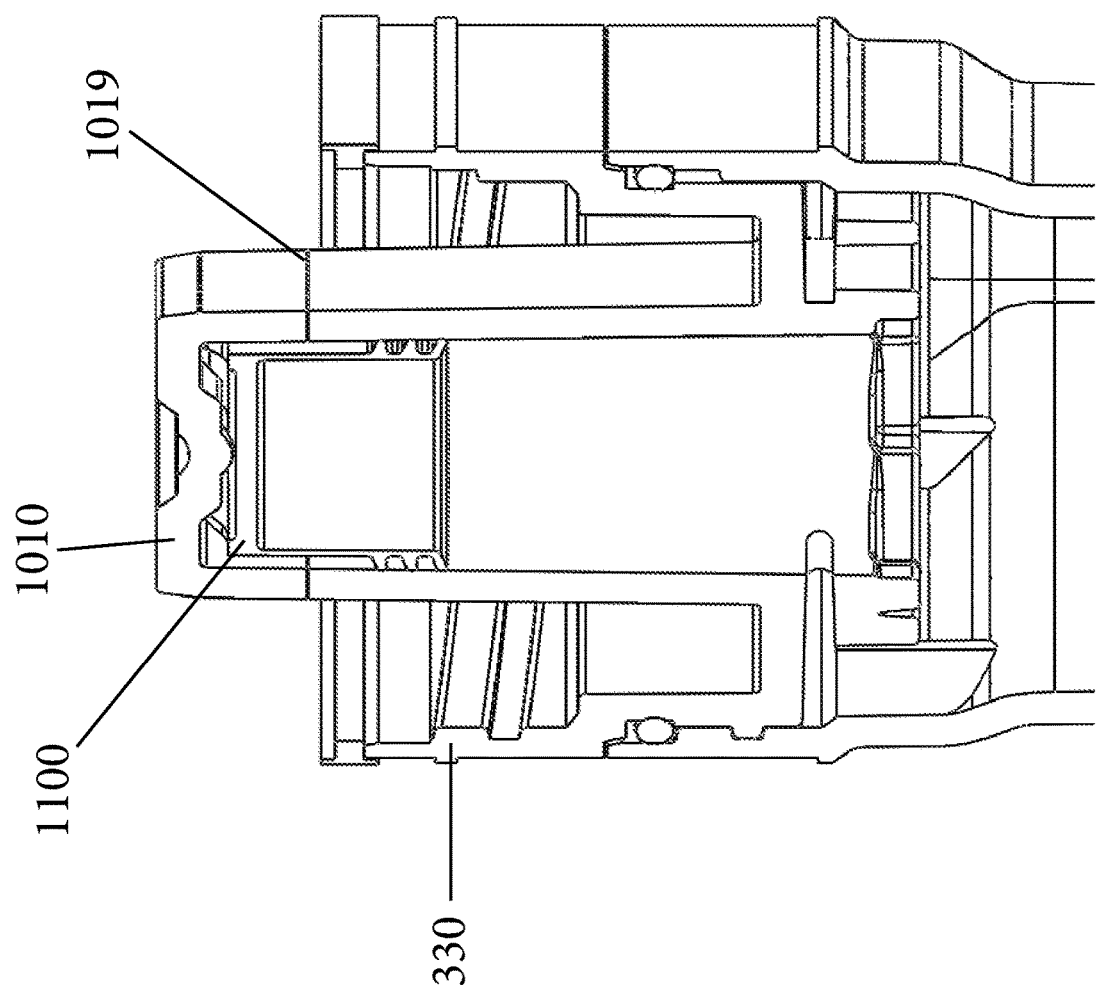

As shown in FIG. 52, the lab technician then spins the spire cutter 2100 one full rotation) (360°), thereby cutting around the perimeter of the spire structure 1010 but not through the spire insert 1100.

As shown in FIG. 52, the wipers 1115 of the spire insert 1100 seal the top of the spire structure 1010 and protect it from coming in contact with fluid (e.g., urine), virtually eliminating the potential for contamination. The wipers 1115 of the spire insert 1100 also serve to locate the top of the spire structure 1010 in the bottom of the spire structure 1010.

Figure 54:
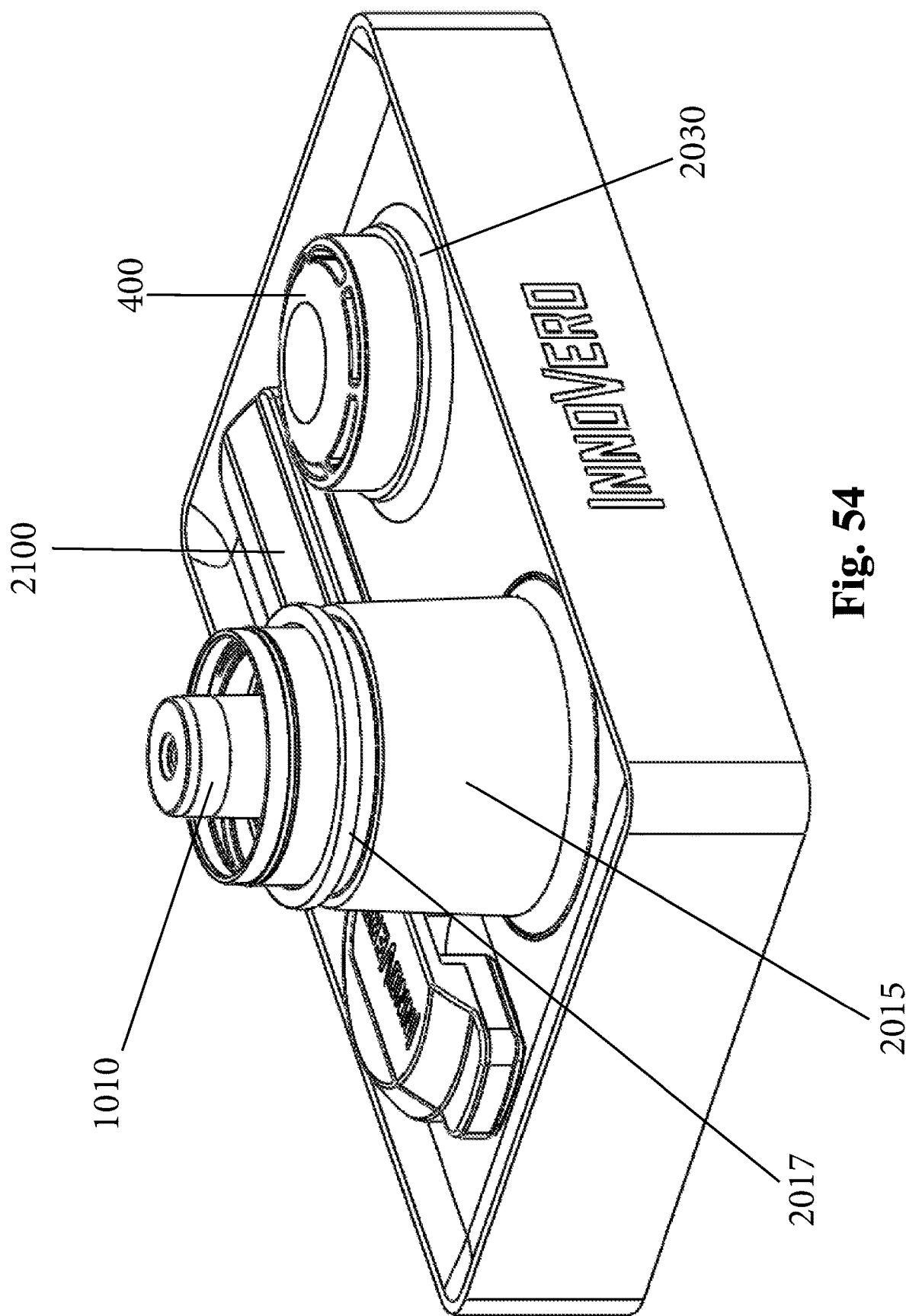

As shown in FIG. 53, the lab technician removes the spire cutter 2100 by sliding it horizontally backward away from the spire structure 1010. The lab tech then returns the spire cutter 2100 to the first recessed portion 2010 as shown in FIG. 54.

Figure 55:
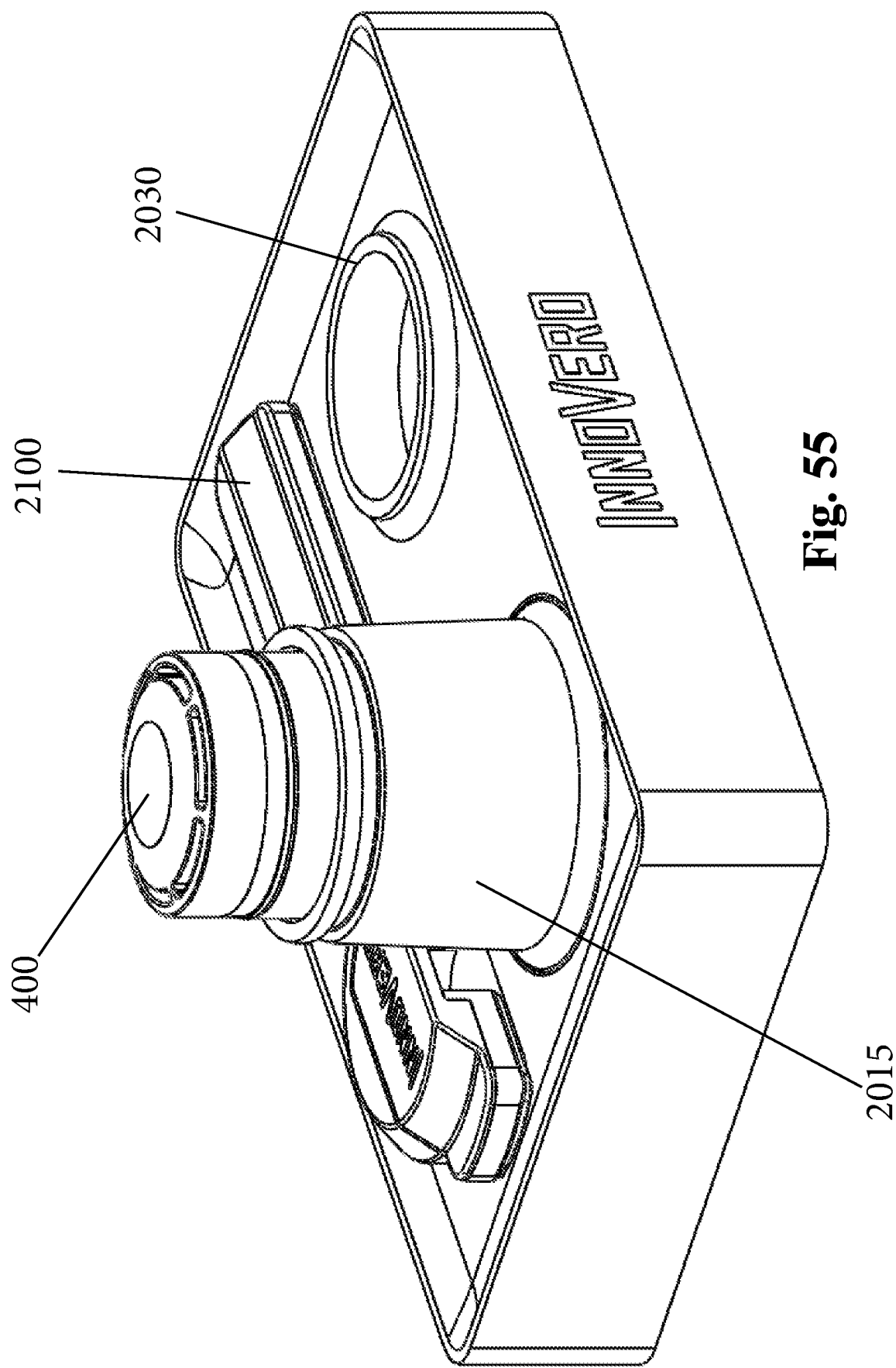

As shown in FIG. 55, with the cap spacer discarded, the lab technician screws the cap 400 back onto the lock ring 330 to engage the press fit between the top of the spire structure 1010 and the underside of the cap 400, thereby effectively creating one unit.

Figure 56:
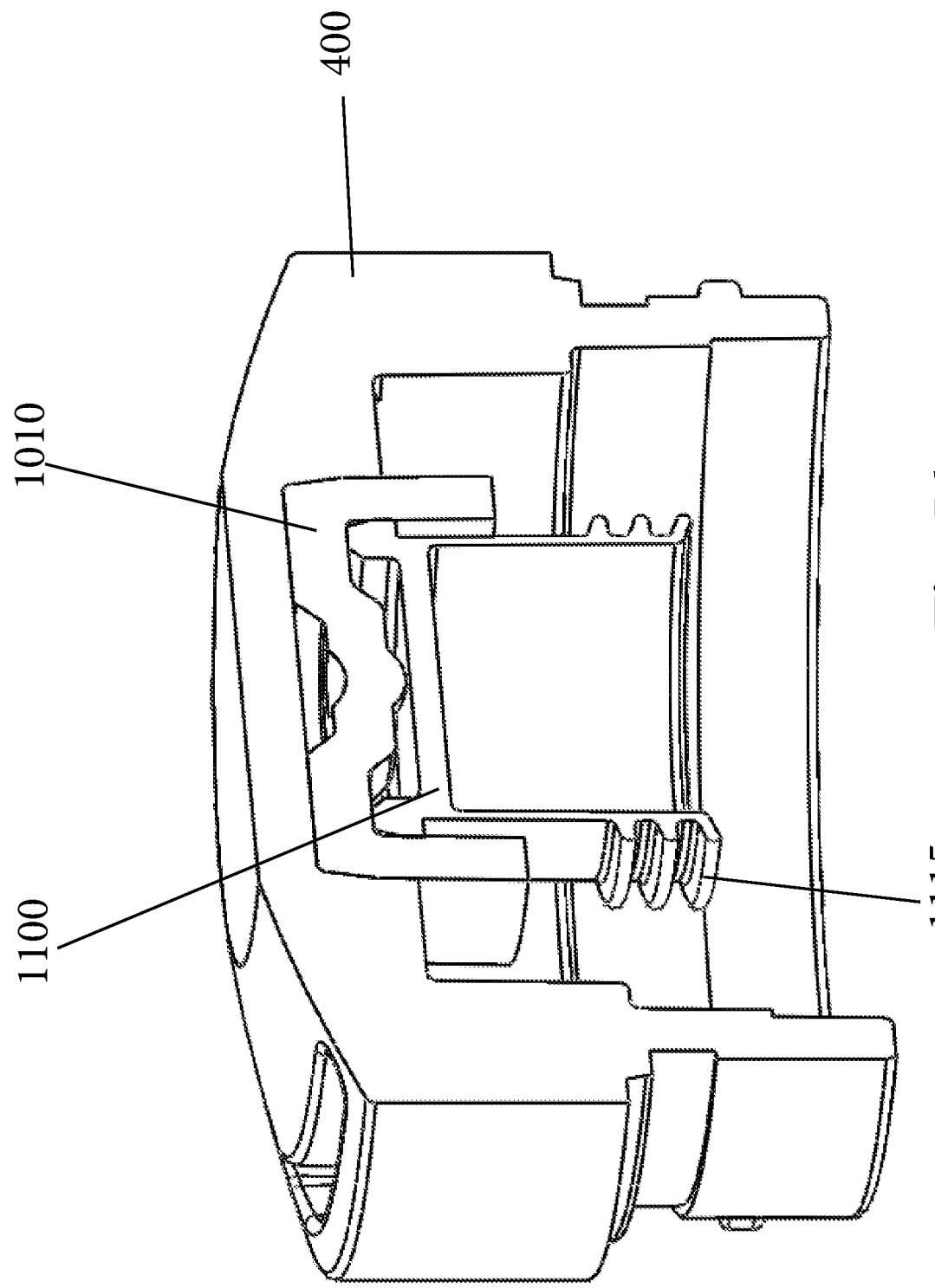

As shown in FIG. 56 and described previously, the spire insert 1100 is press fit into the top of the spire structure 1010 at the factory (manufacturing site) or the like, which is press fit into the underside of the cap 400 after the spire structure 1010 is cut, effectively creating one unit. This eliminates the need for any direct human contact with the spire seal, reducing the chance of cross-contamination during the opening process. Additionally, the bottom of the cap 400 is below the bottom of the spire insert 1100, reducing the chance of cross-contamination if the lab technician sets the cap down.

Figure 57:
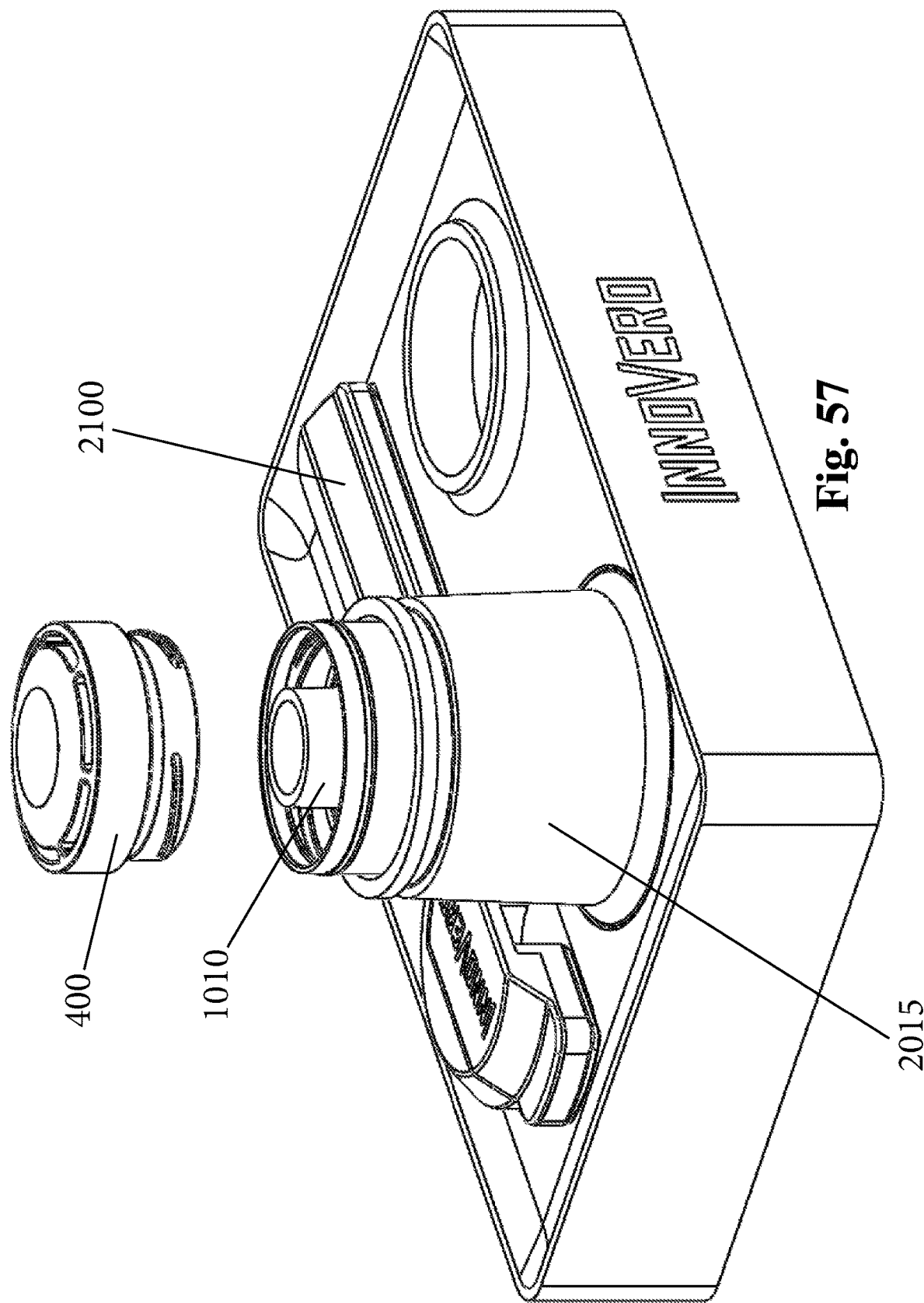

As shown in FIG. 57, after the press fit engagement, the lab technician unscrews the cap assembly (with the top of the spire structure 1010 and the spire insert 1100) to access to the sample inside.

Figure 58:
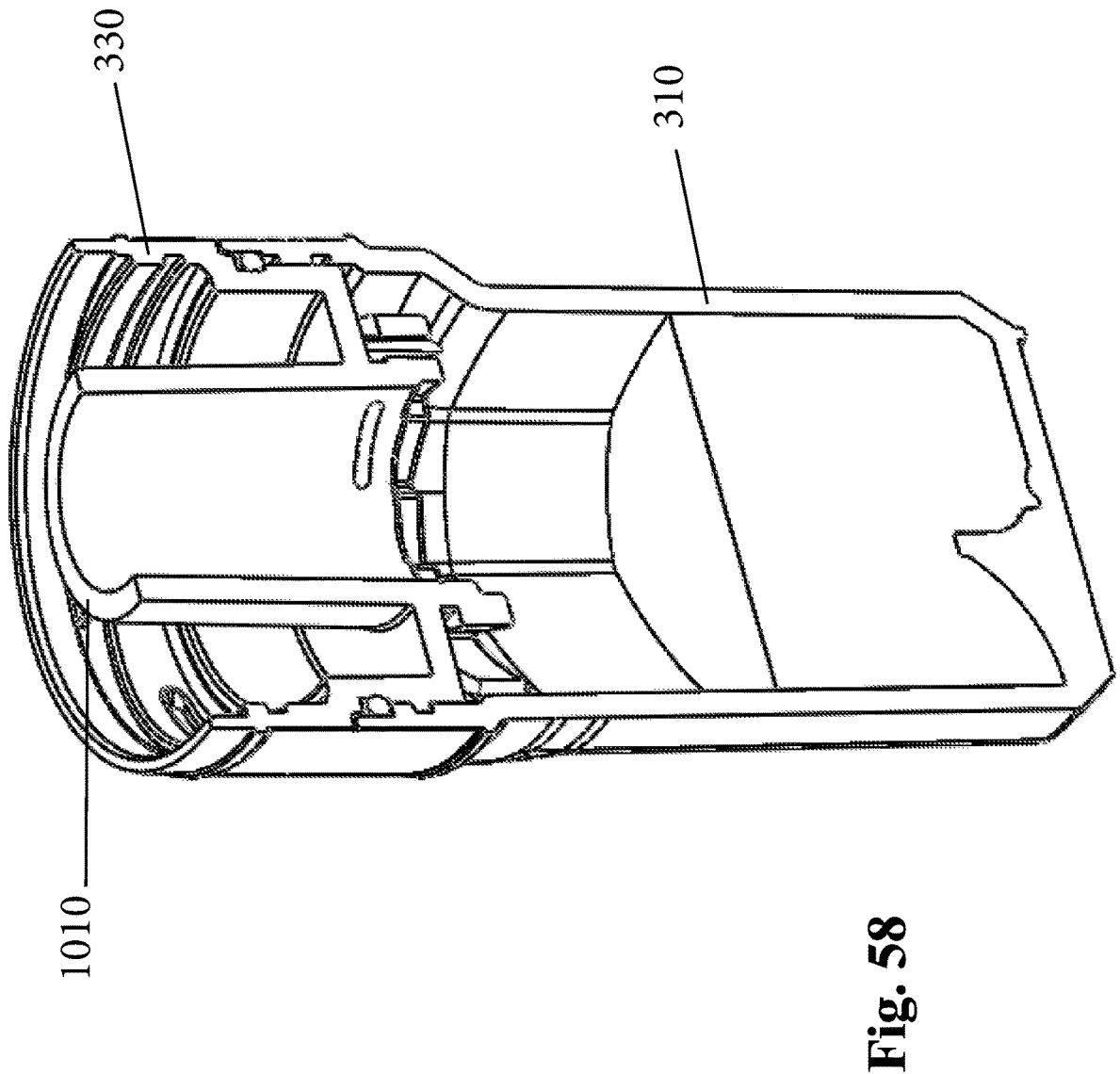

As shown in FIG. 58, the lab technician can aliquot via pouring or pipetting.

Figure 59:
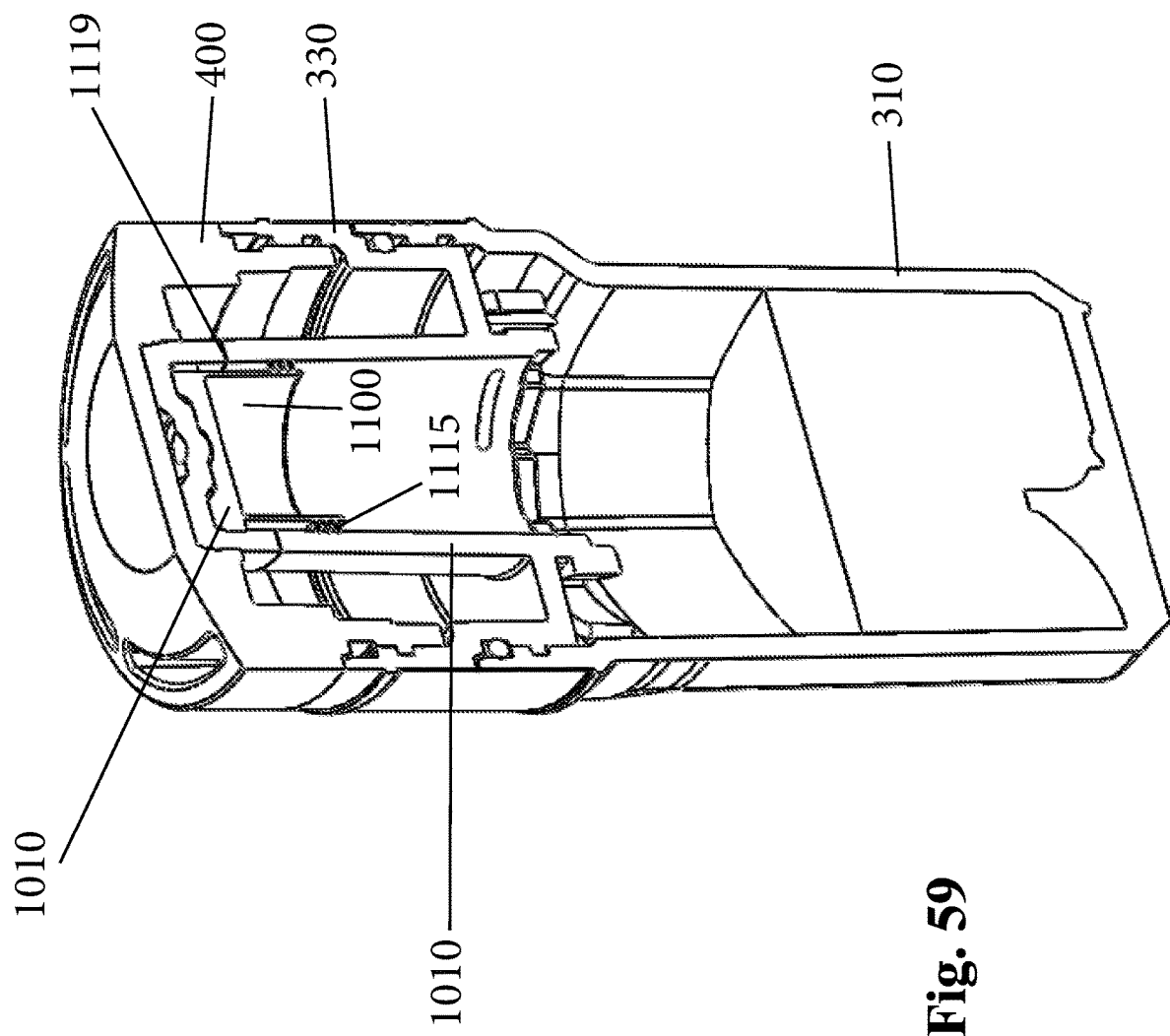

As shown in FIG. 59, after the sample has been accessed, the cap assembly 400 can be screwed back into place. The wipers 1115 on the bottom of the spire insert 1100 seal against the inside of the spire structure 1010.

Figure 60:
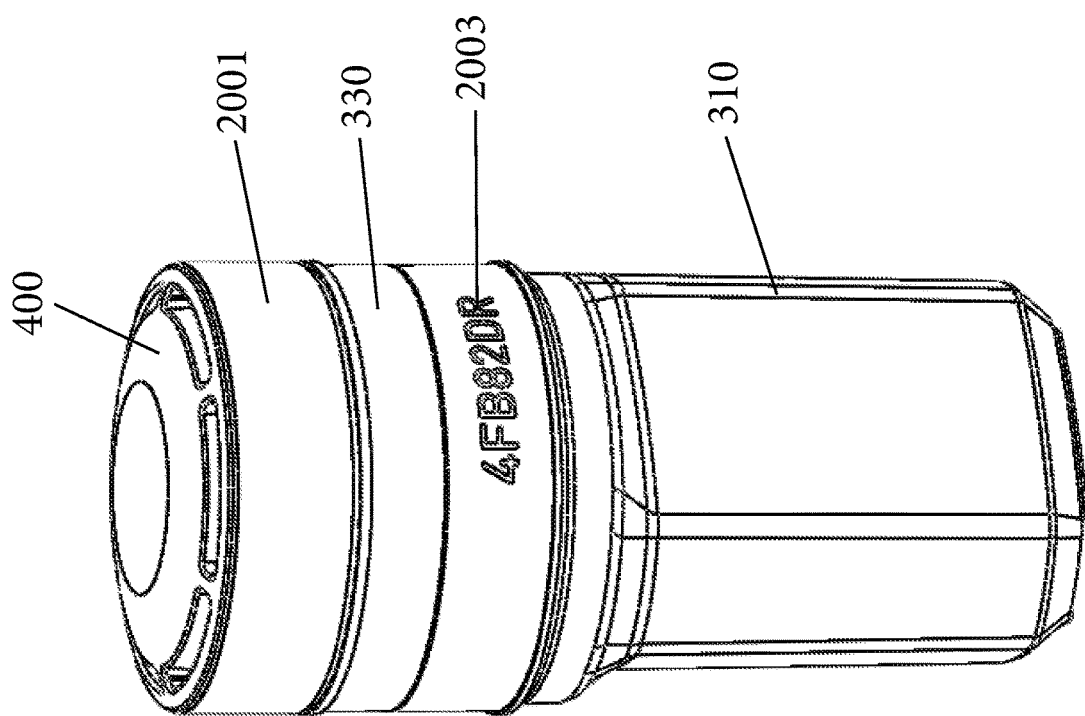

FIG. 60 illustrates that if necessary, the lab tech can attach an optional security label 2001 to cover the entire circumference of the seam between the cap 400 and the lock ring 330, securing the sample for transport or storage. It will be understood that the security label 2001 can be a transparent label except for identification indicia 2003 and therefore, in FIG. 60, the label 2001 can cover the ring 330 and side of the cap 400.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. A system for opening a secure specimen sample bottle comprising:
    a base having a first area and a first raised hollow portion for receiving and holding the specimen sample bottle, the first raised hollow portion having an arcuate shaped groove formed along an outer surface thereof; and
    a cutter for cutting a first portion of the specimen sample bottle, the cutter having a handle at a first end, an opposing second end portion that receives the first portion of the specimen sample bottle, and a blade for cutting the first portion of the specimen sample bottle, the second end portion having a flange with a raised arcuate shaped rail formed along an inner surface of the flange, the raised arcuate shaped rail being received within the groove to couple the cutter to the first raised hollow portion during performance of a cutting operation;
    wherein the blade is spaced above and lies in a different plane than the raised arcuate shaped rail and at least one end of the blade is disposed radially inside of the raised arcuate shaped rail.
2. The system of claim 1, wherein the groove comprises a continuous groove that extends about an entire circumference of the outer surface of the first raised hollow portion and the raised rail has an arcuate shape to permit full rotation of the cutter about the first raised hollow portion.
3. The system of claim 1, wherein the blade is disposed within a plane that is parallel to a plane containing the raised arcuate shaped rail.
4. A system for opening a secure specimen sample bottle comprising:
    a base having a first area and a first raised hollow portion for receiving and holding the specimen sample bottle, the first raised hollow portion having an arcuate shaped groove formed along an outer surface thereof; and
    a cutter for cutting a first portion of the specimen sample bottle, the cutter having a handle at a first end, an opposing second end portion that receives the first portion of the specimen sample bottle, and a blade for cutting the first portion of the specimen sample bottle, the second end portion having a flange with a raised arcuate shaped rail formed along an inner surface of the flange, the raised arcuate shaped rail being received within the groove to couple the cutter to the first raised hollow portion during performance of a cutting operation;
    wherein the base comprises a tray with a floor, the first area being a recessed portion for receiving and holding the cutter and the first raised hollow portion protrudes upwardly from the floor.
5. The system of claim 4, wherein a hollow interior of the first raised hollow portion has a non-circular shape.
6. The system of claim 4, wherein the tray further includes a second raised hollow portion for receiving and holding a removable cap of the specimen sample bottle.
7. A system for opening a secure specimen sample bottle comprising:
    a base in the form of a tray having a first area and a first raised hollow portion for receiving and holding the specimen sample bottle, the first raised hollow portion having a groove formed along an outer surface thereof; and
    a cutter for cutting a first portion of the specimen sample bottle, the cutter having a handle at a first end, an opposing second end portion that receives the first portion of the specimen sample bottle, and a blade for cutting the first portion of the specimen sample bottle, the second end portion having a flange that defines a hollow interior space, with a raised rail being formed along an inner surface of the flange, the raised rail being received within the groove to couple the cutter to the first raised hollow portion during performance of a cutting operation, the blade being located parallel to the raised rail;
    wherein the cutter comprises a hand-held device with the second end portion being an enlarged portion that includes an opening for receiving the first portion of the specimen sample bottle, the opening being located above the hollow interior space, wherein a sharp distal end of the blade protrudes within the opening for cutting the first portion of the specimen sample bottle, the flange being arcuate shaped and located such that the flange surrounds the opening with the raised rail facing the opening.
8. The system of claim 7, wherein the second end portion has an arcuate shaped wall formed along an upper surface of the second end portion with the flange being located along a lower surface of the second end portion.
9. The system of claim 7, wherein the opening is defined by an arcuate shaped inner wall.

10. A system for opening a secure specimen sample bottle comprising:
- a base having a first area and a first raised hollow portion for receiving and holding the specimen sample bottle, the first raised hollow portion having a groove formed along an outer surface thereof; and
- a cutter for cutting a first portion of the specimen sample bottle, the cutter having a handle at a first end, an opposing second end portion that receives the first portion of the specimen sample bottle, and a blade for cutting the first portion of the specimen sample bottle, the second end portion having a flange with a raised rail formed along an inner surface of the flange, the raised rail being received within the groove to couple the cutter to the first raised hollow portion during performance of a cutting operation;
- wherein the cutter comprises a hand-held device with the second end portion being an enlarged portion that includes an opening for receiving the first portion of the specimen sample bottle, wherein a sharp distal end of the blade protrudes within the opening for cutting the first portion of the specimen sample bottle, the flange being arcuate shaped and located such that the flange surrounds the opening with the raised rail facing the opening;
- wherein the cutter has a cover that is secured at the second end portion and covers the opening, the blade being disposed between the cover and an upper surface of the second end portion.

11. The system of claim 10, wherein the upper surface has a raised arcuate shaped wall that defines a distal end region located between a distal end of the handle and the raised arcuate shaped wall, the cover having a stepped construction with a first end portion of the cover being disposed within the distal end region and a second end portion of the cover seating over the raised arcuated shaped wall.

12. A system for opening a secure specimen sample bottle comprising:
- a base having a first area and a first raised hollow portion for receiving and holding the specimen sample bottle, the first raised hollow portion having a groove formed along an outer surface thereof; and
- a cutter for cutting the specimen sample bottle, the cutter having a handle at a first end, an opposing second end portion that receives a top section of the specimen sample bottle, and a blade for cutting the top section of the specimen sample bottle, the second end portion having a flange that defines a cylindrically shaped hollow interior space, the flange having a raised rail formed along an inner surface of the flange, the raised rail being received within the groove to couple the cutter to the first raised hollow portion during performance of a cutting operation, the second end portion further including an opening that is above and opens into the cylindrically shaped hollow interior space, wherein a diameter of the opening is less than a diameter of the cylindrically shaped hollow interior space, the blade extending at least partially into the opening, the cutter further including a cover that covers the blade and the opening.

* * * * *